US009279801B2

(12) United States Patent
Rajaraman et al.

(10) Patent No.: US 9,279,801 B2
(45) Date of Patent: *Mar. 8, 2016

(54) DEVICES, SYSTEMS AND METHODS FOR HIGH-THROUGHPUT ELECTROPHYSIOLOGY

(71) Applicant: AXION BIOSYSTEMS, INC., Atlanta, GA (US)

(72) Inventors: Swaminathan Rajaraman, Atlanta, GA (US); James D. Ross, Decatur, GA (US); Amanda Preyer, Atlanta, GA (US)

(73) Assignee: AXION BIOSYSTEMS, INC., Atlanta, GA (US)

( * ) Notice: Subject to any disclaimer, the term of this patent is extended or adjusted under 35 U.S.C. 154(b) by 34 days.

This patent is subject to a terminal disclaimer.

(21) Appl. No.: 14/279,961

(22) Filed: May 16, 2014

(65) Prior Publication Data
US 2015/0027885 A1  Jan. 29, 2015

Related U.S. Application Data

(60) Provisional application No. 61/858,945, filed on Jul. 26, 2013.

(51) Int. Cl.
*G01N 27/327* (2006.01)
*G01N 33/50* (2006.01)
*G01N 33/483* (2006.01)

(52) U.S. Cl.
CPC ........ *G01N 33/5014* (2013.01); *G01N 33/4836* (2013.01)

(58) Field of Classification Search
CPC .................... G01N 33/4836; G01N 33/48727; G01N 33/48728
See application file for complete search history.

(56) References Cited

U.S. PATENT DOCUMENTS 4,806,432 A   2/1989  Eguchi et al.
5,965,452 A   10/1999 Kovacs
(Continued)

OTHER PUBLICATIONS

Agar, J.C. et al., "Novel PDMS(silicone)-in-PDMS(silicone): Low Cost Flexible Electronics without Metallization," 2010 Electronic Components and Technology Conference, pp. 1226-1230, 2010.
(Continued)

*Primary Examiner* — Alexander Noguerola
(74) *Attorney, Agent, or Firm* — Meunier Carlin & Curfman LLC

(57) ABSTRACT

Electrophysiology culture plates are provided and are formed from a transparent microelectrode array (MEA) plate. The MEA plate comprises a substrate, a first layer and a first insulating layer. The substrate has a plurality of vias extending from an upper to a lower surface, each via being in electrical contact with each of a plurality of contact pads disposed on the lower surface. The first layer is disposed on the upper surface of the substrate and has a plurality of MEA arrays in in electrical communication with at least a first routing layer. Each MEA array comprises a plurality of reference electrodes and a plurality of microelectrodes and the first routing layer is in electrical communication with a select number of the plurality of vias. A first insulating layer is disposed on the first layer. The MEA plate is joined to a biologic culture plate having a plurality of culture wells such that each culture well defines an interior cavity having a bottom surface that is at least partially transparent and in positioned in registration with a select optical port. The MEA plate is coupled to the biologic culture well plate such that each MEA array is operatively coupled to one culture well wherein each microelectrode and each reference electrode are in electrical communication with the interior cavity through the bottom surface of the culture well.

30 Claims, 23 Drawing Sheets

(56) References Cited

U.S. PATENT DOCUMENTS

| | | | |
|---|---|---|---|
| 6,051,422 | A | 4/2000 | Kovacs et al. |
| 6,132,683 | A | 10/2000 | Sugihara et al. |
| 6,315,940 | B1 | 11/2001 | Nisch et al. |
| 6,352,853 | B1 | 3/2002 | King et al. |
| 6,376,233 | B1 | 4/2002 | Wolf et al. |
| 6,969,449 | B2 | 11/2005 | Maher et al. |
| 7,169,609 | B2 | 1/2007 | Negulescu et al. |
| 7,192,752 | B2 | 3/2007 | Xu et al. |
| 7,267,751 | B2 | 9/2007 | Gelbart et al. |
| 7,470,533 | B2 | 12/2008 | Xu et al. |
| 7,981,362 | B2 * | 7/2011 | Glezer et al. .............. 422/50 |
| 8,227,223 | B2 | 7/2012 | Giaever et al. |
| 8,361,385 | B2 | 1/2013 | Glezer et al. |
| 8,420,363 | B2 | 4/2013 | Wang et al. |
| 8,460,921 | B2 | 6/2013 | Gross |
| 2002/0192120 | A1 | 12/2002 | DeSilets et al. |
| 2005/0006234 | A1 | 1/2005 | Hassibi |
| 2006/0018833 | A1 | 1/2006 | Murphy et al. |
| 2006/0057771 | A1 | 3/2006 | Kovacs et al. |
| 2007/0178579 | A1 | 8/2007 | Ross et al. |
| 2009/0004754 | A1 | 1/2009 | Oldenburg |
| 2009/0297913 | A1 | 12/2009 | Zhang et al. |
| 2010/0120626 | A1 | 5/2010 | Ross et al. |
| 2013/0123139 | A1 | 5/2013 | Kim et al. |

OTHER PUBLICATIONS

American National Standards Institutes, Inc. (ANSI), Society for Laboratory Automation and Screening (SLAS), Footprint Dimensions, 2004.

American National Standards Institutes, Inc. (ANSI), Society for Laboratory Automation and Screening (SLAS), Height Dimensions, 2004.

American National Standards Institutes, Inc. (ANSI), Society for Laboratory Automation and Screening (SLAS), Bottom Outside Flange Dimensions, 2004.

American National Standards Institutes, Inc. (ANSI), Society for Laboratory Automation and Screening (SLAS), Well Positions, 2004.

American National Standards Institutes, Inc. (ANSI), Society for Laboratory Automation and Screening (SLAS), Well Bottom Elevation, 2011.

Bai, Q. et al., "Single-Unit Neural Recording with Active Microelectrode Arrays", IEEE Transactions on Biomedical Engineering, vol. 48, No. 8, pp. 911-920, 2001.

Blum, R.A. et al., "An Integrated System for Simultaneous, Multichannel Neuronal Stimulation and Recording", IEEE Transactions on Circuits and Systems, vol. 54, No. 12, pp. 2608-2618, 2007.

Brown, E.A. et al., "Stimulation and Recording of Neural Tissue, Closing the Loop on the Artifact", IEEE International Symposium on Circuits and Systems, pp. 356-359, 2008.

Brown, E.A. et al., "Stimulus-Artifact Elimination in a Multi-Electrode System", IEEE Transactions on Biomedical Circuits and Systems, vol. 2, No. 1, pp. 10-21, 2008.

Cetiner, B.A. et al., "Monolithic Integration of RF MEMS Switches with a Diversity Antenna on PCB Substrate", IEEE Transactions on Microwave Theory and Techniques, vol. 51, No. 1, pp. 332-335, 2003.

Cullen, D.K. et al., "Microfluidic engineered high cell density three-dimensional neural cultures", Journal of Neural Engineering, vol. 4, pp. 159-172, 2007.

Van Dijk, J.P. et al., "Corrigendum to 'Motor unit number estimation using high-density surface electromyography'", Clinical Neurophysiology, vol. 119, p. 2416, 2008.

French, R.H. et al., "Optical properties of polymeric materials for conentrator photovoltaic systems", Solar Energy Materials & Solar Cells, vol. 95, pp. 2077-2086, 2011.

Ghodsian, B. et al., "Development of RF-MEMS Switch on PCB Substrates With Polyimide Planarization", IEEE Sensors Journal, vol. 5, No. 5, pp. 950-955, 2005.

Giovangrandi, L. et al., "Low-cost microelectrode array with integrated heater for extracellular recording of cardiomyocyte cultures using commercial flexible printed circuit technology", Sensors and Actuators B, vol. 113, pp. 545-554, 2006.

Gong, J. et al., "Two-Dimensional Digital Microfluidic System by Multi-Layer Printed Circuit Board", 18th IEEE International Conference on Micro Electro Mechanical Systems, pp. 726-729, 2005.

Heuschkel, M.O. et al., "A three-dimensional multi-electrode array for multi-site stimulation and recording in acute brain slices", Journal of Neuroscience Methods, vol. 114, pp. 135-148, 2002.

Joung, Y.H. et al., "Inter-substrate microstructure formation by electroplating bonding technology", Journal of Micromech. and Microeng., vol. 18, 2008.

Guo, L. et al., "A Low-Cost, Easy-Fabricating Stretchable Microneedle-Electrode Array for Intramuscular Recording and Stimulation", Proceedings of the 5th International IEEE EMBS Conference on Neural Engineering, pp. 562-565, 2011.

Guo, L. et al., "A PDMS-Based Integrated Stretchable Microelectrode Array (isMEA) for Neural and Muscular Surface Interfacing," IEEE Trans. on Biomed. Circuits and Syst., vol. 7, No. 1, pp. 1-10, Feb. 2013.

Lorenz, H. et al., "High-aspect-ratio, ultrathick, negative-tone near-UV photoresist and its applications for MEMS", Sensors and Actuators A, vol. 64, pp. 33-39, 1998.

Lorenz, H. et al., "Fabrication of photoplastic high-aspect ratio microparts and micromolds using SU-8 UV resist", Microsystem Technologies, vol. 4, pp. 143-146, 1998.

Metz, S. et al., "Microelectrodes with three-dimensional structures for improved neural interfacing", 2001 Proceedings of the 23rd Annual EMBS International Conference, IEEE, pp. 765-768, 2001.

Oka, H. et al., "A new planar multielectrode array for extracellular recording: application to hippocampal acute slice", Journal of Neuroscience Methods, vol. 93, pp. 61-67, 1999.

Rajaraman, S. et al., "Microfabrication technologies for a coupled three-dimensional microelectrode, microfluidic array", J. Micromech. Microeng., vol. 17, pp. 163-171, 2007.

Rajaraman, S. et al., "Three-Dimensional Metal Transfer Micromolded Microelectrode Arrays (MEAs) for In-vitro Brain Slice Recordings", Solid-State Sensors, Actuators and Microsystems Conference, 2007.

Ramadoss, R. et al., "RF-MEMS Capacitive Switches Fabricated Using Printed Circuit Processing Techniques", Journal of Microelectromechanical Systems, vol. 15, No. 6, pp. 1595-1604, 2006.

Rennaker, R.L. et al., "An economical multi-channel cortical electrode array for extended periods of recording during behavior", Journal of Neuroscience Methods, vol. 142, pp. 97-105, 2005.

Ross, J.D. et al., "Multielectrode Impedance Tuning: Reducing Noise and Improving Stimulation Efficacy", Proceedings of the 26th Annual Conference of the IEEE EMBS, pp. 4115-4117, 2004.

"Toxicity Testing in the 21st Century: A Vision and a Strategy", The National Research Council, National Academies Press, 2007.

Wise, K., "Silicon Microsystems for Neuroscience and Neural Prostheses: Interfacing with the Central Nervous System at the Cellular Level", IEEE Engineering in Medicine and Biology Magazine, pp. 22-29, 2005.

Yaradanakul, A. et al., "Uncooled Infrared Microbolometers on a Flexible Substrate", IEEE Transactions on Electron Devices, vol. 49, No. 5, pp. 930-933, 2002.

Morin, F. et al., "Constraining the connectivity of neuronal networks cultured on micro-electrode arrays with microfluidic techniques: A step towards neuron-based functional chips," Biosensors and Bioelectronics, vol. 21, pp. 1093-1100, 2006.

French, R.H. et al., "Optical Properties of Materials for Concentrator Photovoltaic Systems," Photovoltaic Specialists Conference (PSVC), 2009 34th IEEE, pp. 394-399, 2009.

Dunlop, J. et al., "High-throughput electrophysiology: an emerging paradigm for ion-channel screening and physiology," Nature Reviews Drug Discovery, vol. 7, pp. 358-368, 2008.

International Search Report and Written Opinion of the International Searching Authority for PCT/US2014/039780, mailed Sep. 30, 2014.

* cited by examiner

FIG. 15

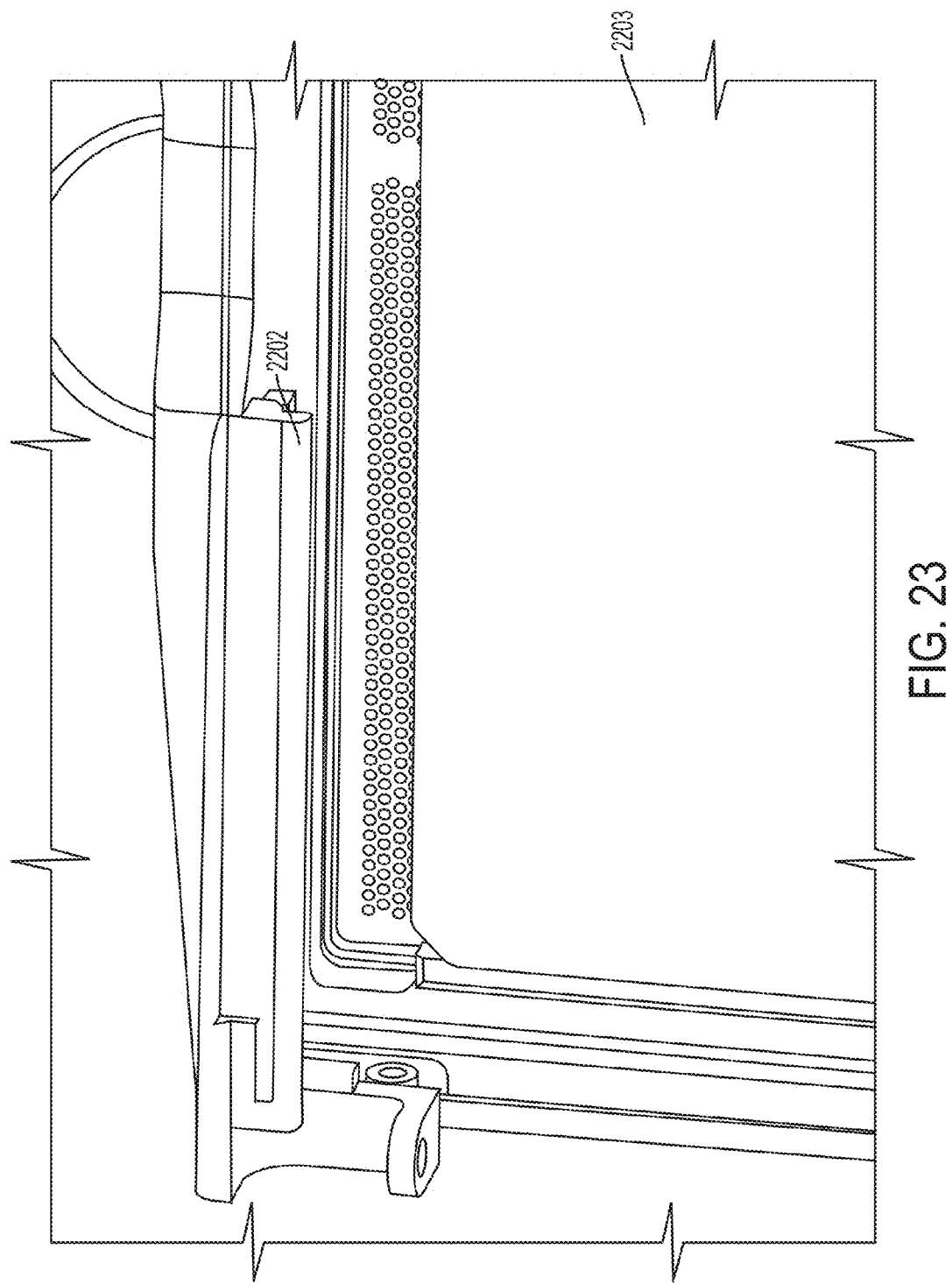

DEVICES, SYSTEMS AND METHODS FOR HIGH-THROUGHPUT ELECTROPHYSIOLOGY

CROSS-REFERENCE TO RELATED APPLICATION

This application claims the benefit of U.S. Provisional Application No. 61/858,945, filed Jul. 26, 2013, which is hereby incorporated herein by reference in its entirety.

BACKGROUND

1. The Field of the Invention

Implementations described herein relate generally to high-throughput electrophysiology culture system and, more particularly, to an electrophysiology culture system with a culture plate having an integrated monolithic microelectrode array plate.

2. Related Art

In vitro electrophysiology culture systems having microelectrode arrays (MEAs) can provide important insights into networks of electrically active cells. MEA-based electrophysiology culture systems can be configured to concurrently monitor single cell and network level activity over extended periods of time and without affecting the cell culture under investigation. Since their instrumental role in the 1993 landmark discovery of spontaneous waves in a developing retina, the variety and scope of MEA-based electrophysiology applications have dramatically expanded. Recently, for example, MEA-based electrophysiology culture systems have been used to investigate the suppression of epileptic activity and in the study of novel plasticity mechanisms in cultured neural networks. Advances in cell culture preparations have similarly led to applications for MEA-based electrophysiology culture systems in the fields of drug screening, safety pharmacology, and biosensing.

Present day MEA-based electrophysiology culture systems are typically designed around small-footprint, single-well devices. However, the complete analysis of complex cellular systems and processes can require repeated experiments. The number of experiments can increase quickly when considering multiple variables, such as stimulus size, compound type, dosage strength and the like. Thus, the small-scale format of traditional MEA systems presents problems due to excessive experimental and statistical sizes, whereby the serial nature of these devices can render even basic investigations time and cost prohibitive. As one illustrative example, a researcher examining the effect of pythrethroids on two-hour spontaneous activity recordings can require 8 doses of permethrin, with an N of 6 for each dose. With traditional MEA-based electrophysiology culture systems, this very simple experiment can require over $5,000 in MEA-based electrophysiology culture plates (or "MEA culture plate") and 50 to 60 man-hours. The time investment can further increase with the logistics of culturing, maintaining, and testing dozens of individual specimen.

Thus, design of a high-throughput MEA culture plate is highly desirable. However, conventional manufacturing techniques fall short of enabling their manufacture by merely scaling up a conventional design. For high-throughput investigations, large-area, American National Standards Institute (ANSI)/Society for Lab Automation and Screening (SLAS)-compliant plates can be important as industry standard compliance can provide compatibility with other high-throughput instrumentation such as plate readers and robotics handlers. Conventional MEA culture plates, some of which can be subdivided into a small number of wells (e.g., about 6), can cost from about $150 to about $500 and are not easily scaled to high well count plates without prohibitive manufacturing costs. Specifically, the development of an ANSI/SLAS-compliant, high-throughput MEA culture plate presents two major challenges: (1) ensuring 100% yield of widely distributed micro-scale electrodes and (2) developing cost-effective manufacturing processes to provide inexpensive high-throughput MEA culture plates. The microfabrication industry has traditionally addressed these issues by fabricating thousands of micro-scale devices in parallel and then individualizing each unit, with the results of reducing the per-unit cost of each device and ensuring that non-working units can quickly be identified and discarded. The working units are then packaged using wafer-level packaging technologies or individual unit-level technologies that have been optimized for cost-effectiveness. However, for high-throughput MEA plate fabrication, the plate size is much greater than traditional micro-scale devices, increasing the likelihood that a single microelectrode may fail, rendering the entire plate a non-working unit. Additionally, if only single plate can be microfabricated on one wafer, the cost advantage is lost versus the batch fabrication of micro-scale-sized devices described above.

Thus, broad access to neural information along with the minimally invasive nature of a MEA-based electrophysiology culture systems renders them a potentially valuable tool for discovery. However, the throughput of MEA-based electrophysiology culture systems needs to increase to keep pace with the requirements of today's researchers. Accordingly, a need exists for improved MEA-based electrophysiology culture systems that provide for high-throughput applications and reliable large-area microfabrication methods to manufacture the MEA plates and, ultimately, the assembled MEA-based electrophysiology culture plates.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, the present disclosure describes an electrophysiology culture plate having an ANSI or SLAS-compliant format comprising a biologic culture plate coupled to a monolithic MEA plate. A monolithic MEA plate can have a plurality of layers having electrodes, electrode routing and vias that ultimately provide for electrical communication between the culture well contents and an electronics unit.

In another aspect, the present disclosure provides for an electrophysiology culture system comprising an electrophysiology culture plate and an electronics unit configured to stimulate at least one cell and immediately record the response after stimulation.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate aspects and together with the description, serve to explain the principles of the methods and systems.

FIG. 15 is a graph illustrating the RMS noise of a single well in an exemplary electrophysiology culture plate of the present disclosure.

FIG. 23 is an enlarged view of the clamping mechanism depicted in FIG. 22.

DETAILED DESCRIPTION

Figure 1:
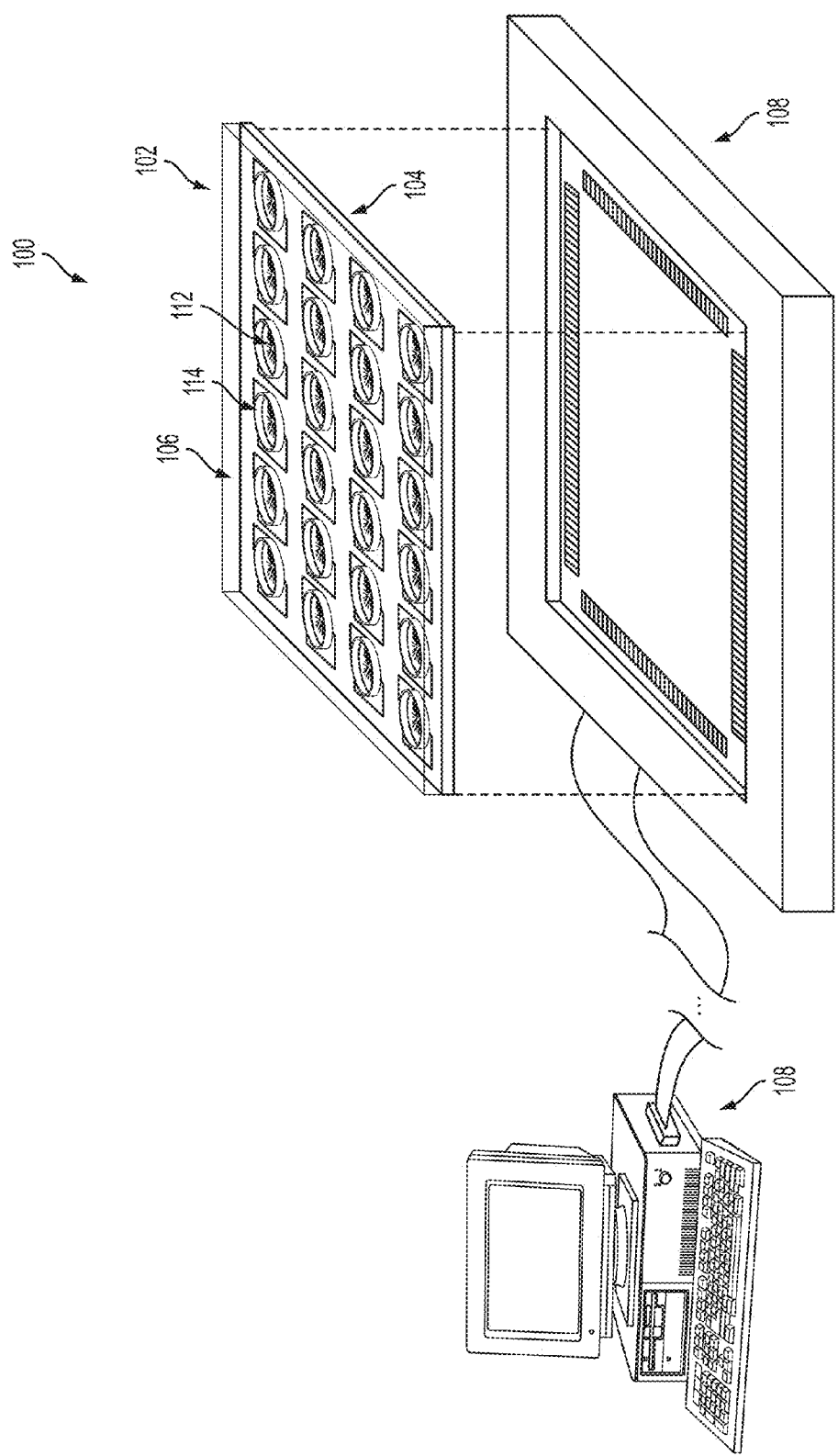
FIG. 1 is a schematic drawing depicting one implementation of a high throughput electrophysiology culture system of the present disclosure.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of electrophysiology culture systems and microelectromechanical systems (MEMS) have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be predefined it is understood that each of these additional steps can be predefined with any specific aspect or combination of aspects of the disclosed methods.

Implementations described herein are directed toward devices, systems and methods for high-throughput electrophysiology. More particularly, the present disclosure is directed to an electrophysiology culture system with a culture plate having an integrated monolithic microelectrode array plate. For example, one or more implementations described herein provide for an electrophysiology culture plate comprising a monolithic MEA plate having a plurality of MEAs and a biologic culture plate having a plurality of culture wells wherein the MEA plate underlies and is coupled to the culture well plate such that each MEA is operatively coupled to one culture well of the plurality of culture wells. In other aspects, the present disclosure is directed to an electronics unit configured to receive the electrophysiology culture plate and, in yet other aspects, to mechanical features provided on both the electrophysiology culture plate and the electronics unit to facilitate placement and advantageous operational modalities of the electrophysiology culture system.

Reference will now be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

High-throughput screening (HTS) tools make use of multiwell biologic culture plates that follow exacting guidelines established by the Society for Lab Automation and Screening (SLAS) and the American National Standards Institute (ANSI). These standards are adhered to by all HTS supporting equipment such as, for example and without limitation, plate readers, robotic handlers, liquid handling devices and the like. Compliance with these standards can enable a high-throughput MEA platform to achieve full potential, as it leverages existing high-throughput infrastructure including the automation of media exchanges and compound delivery. Adherence to the standard, however, requires defining micro-scale structures across a single, large-area plate, which, in turn, can dramatically escalate costs.

Implementations disclosed herein comprise an electrophysiology culture plate assembly and electronics unit docking design based on a vertically integrated footprint constrained by the outer dimensions of the ANSI/SLAS microtiter plate format. The high-throughput electrophysiology culture plate can comprise a multiwall biologic culture plate integrated with an MEA plate. In one aspect, cost-effective, scalable technologies to address these problems are disclosed. In a further aspect, 1-, 6-, 12-, 24-, 48-, 96- and other standard well configuration MEAs on a single monolithic substrate along with their manufacture are disclosed. In some aspects, innovations in inexpensive, standard technologies such as injection molding, die cutting and laser cutting are leveraged to enable modular assembly of these electrophysiology culture well plates.

In the following description, numerous specific details are set forth in order to provide a thorough understanding described herein. It will be obvious, however, to one skilled in the art that the present disclosure may be practiced without these specific details. In other instances, well-known aspects of electrophysiology culture systems and microelectromechanical systems have not been described in particular detail in order to avoid unnecessarily obscuring aspects of the disclosed implementations.

Turning now to FIG. 1, an implementation of one exemplary aspect of a high-throughput electrophysiology culture system 100 is illustrated. An electrophysiology culture plate 102 can comprise a monolithic MEA plate 104 integrated with a biologic culture plate 106, and electronics 108 together with software configured to stimulate a cell culture via the electrophysiology culture plate to evoke a response and to record data. The electrophysiology culture plate can comprise a plurality of culture wells configured to culture electroactive cells. A grid of tightly spaced microelectrodes 112 configured to extracellularly interface with the cultured cells is operatively associated with each culture well 114. Each electrode can be configured to record electrical activity from nearby neurons and electrically stimulate those cells. This technique can provide an extracellular, label free method for examining both individual neuronal behavior and overall network activity, optionally, simultaneously. Mechanical features can also be provided that operate to couple the MEA culture well plate to the electronic unit. In a further aspect, these mechanical features can be configured so as not to interfere with topside access to the electrophysiology culture plate. In another aspect, the electronics unit can be used amplify and filter the low amplitude extracellular signals captured by both the microelectrodes and reference electrodes and, in other aspects, provide user directed stimulation to the cells. In further aspects, the electronics unit can convert the analog electrode signals received from the cells into data that can be used and manipulated by the computer software, while minimizing the amount of noise injected into the very low amplitude signals that are measured (i.e., extracellular recordings).

Figure 2:
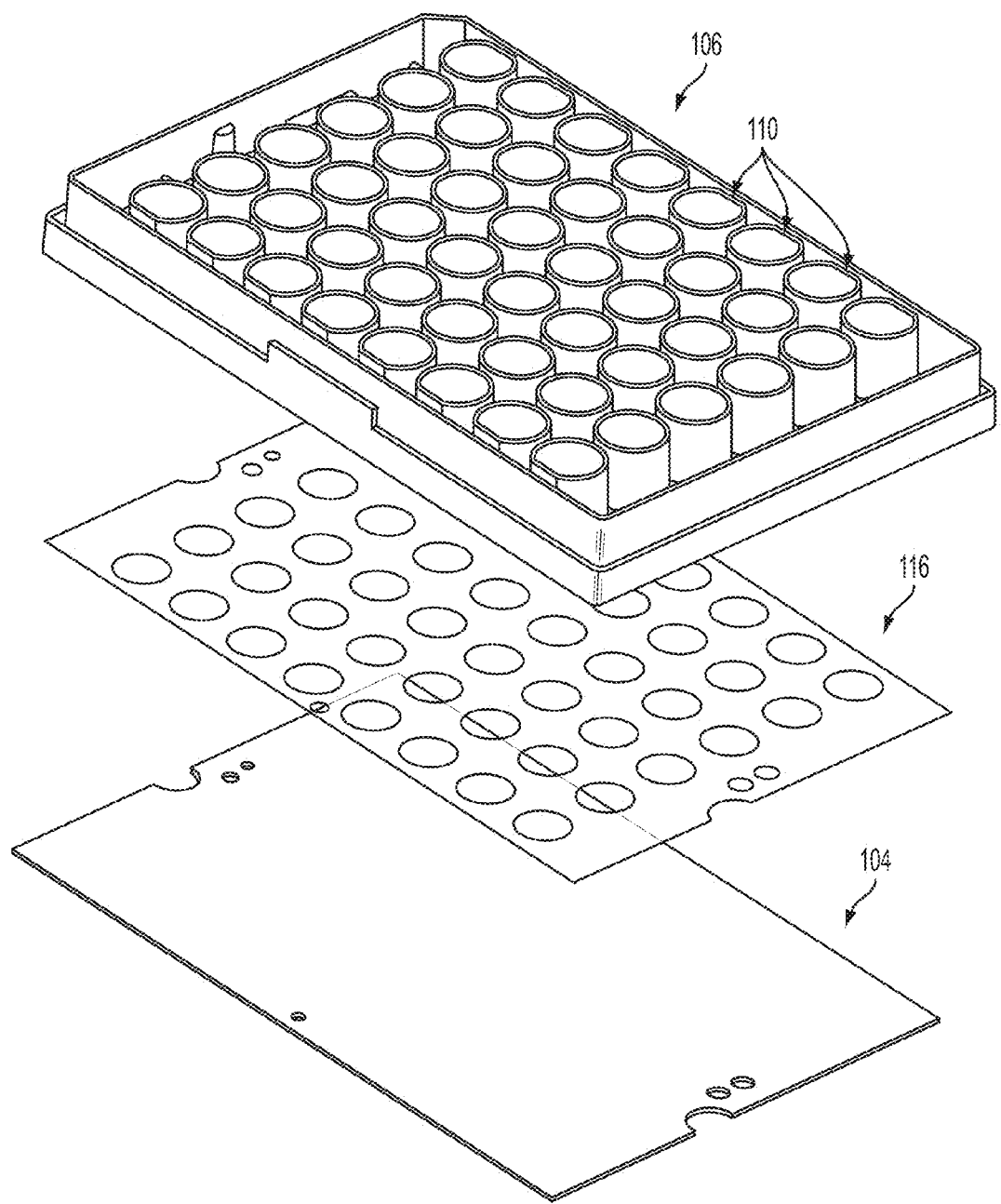
FIG. 2 depicts an exploded perspective view of one implementation of an electrophysiology culture plate of the present disclosure.
Figure 3:
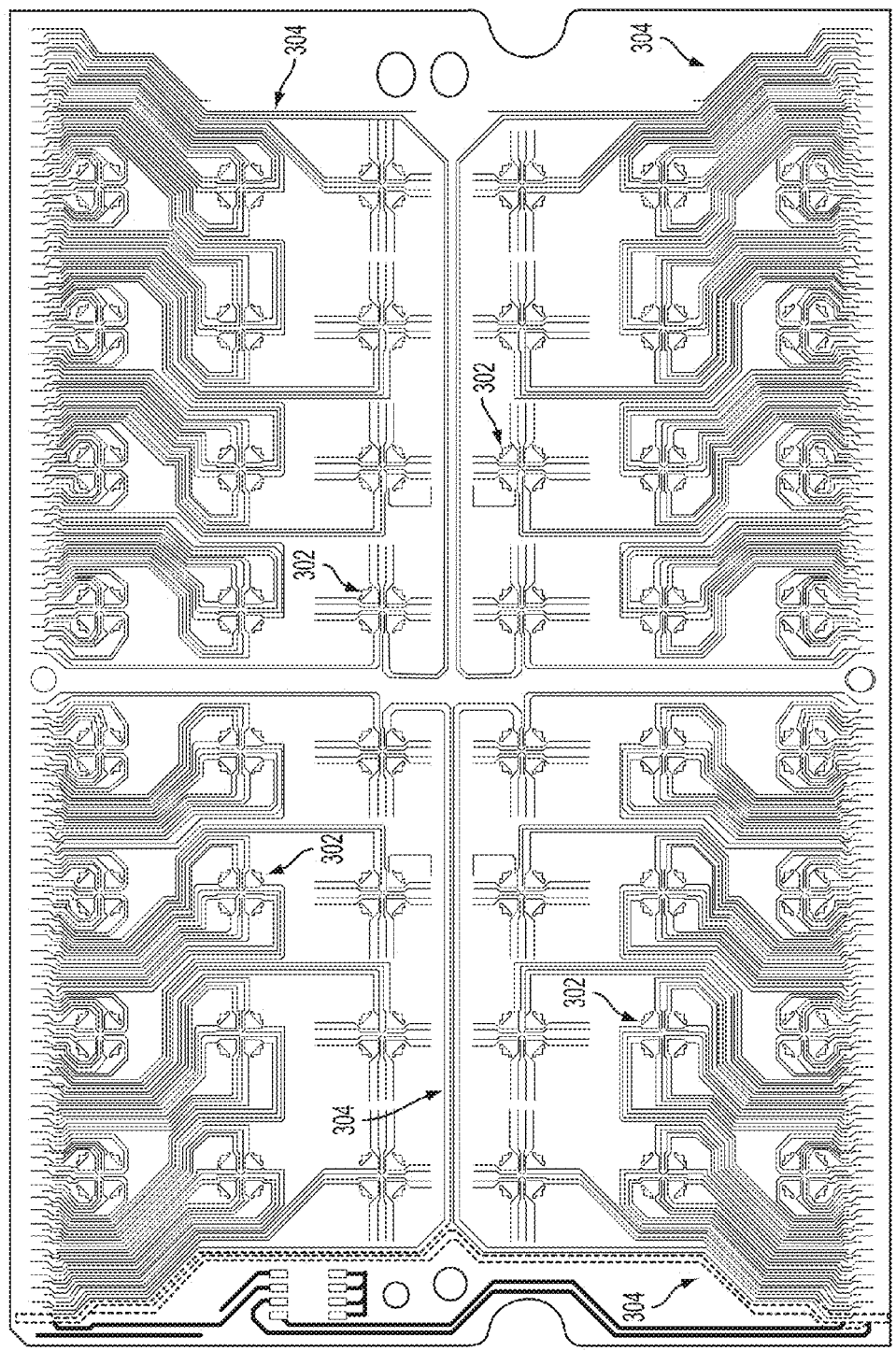
FIG. 3 depicts one exemplary implementation of a first layer of the monolithic microelectrode array plate.
Figure 4:
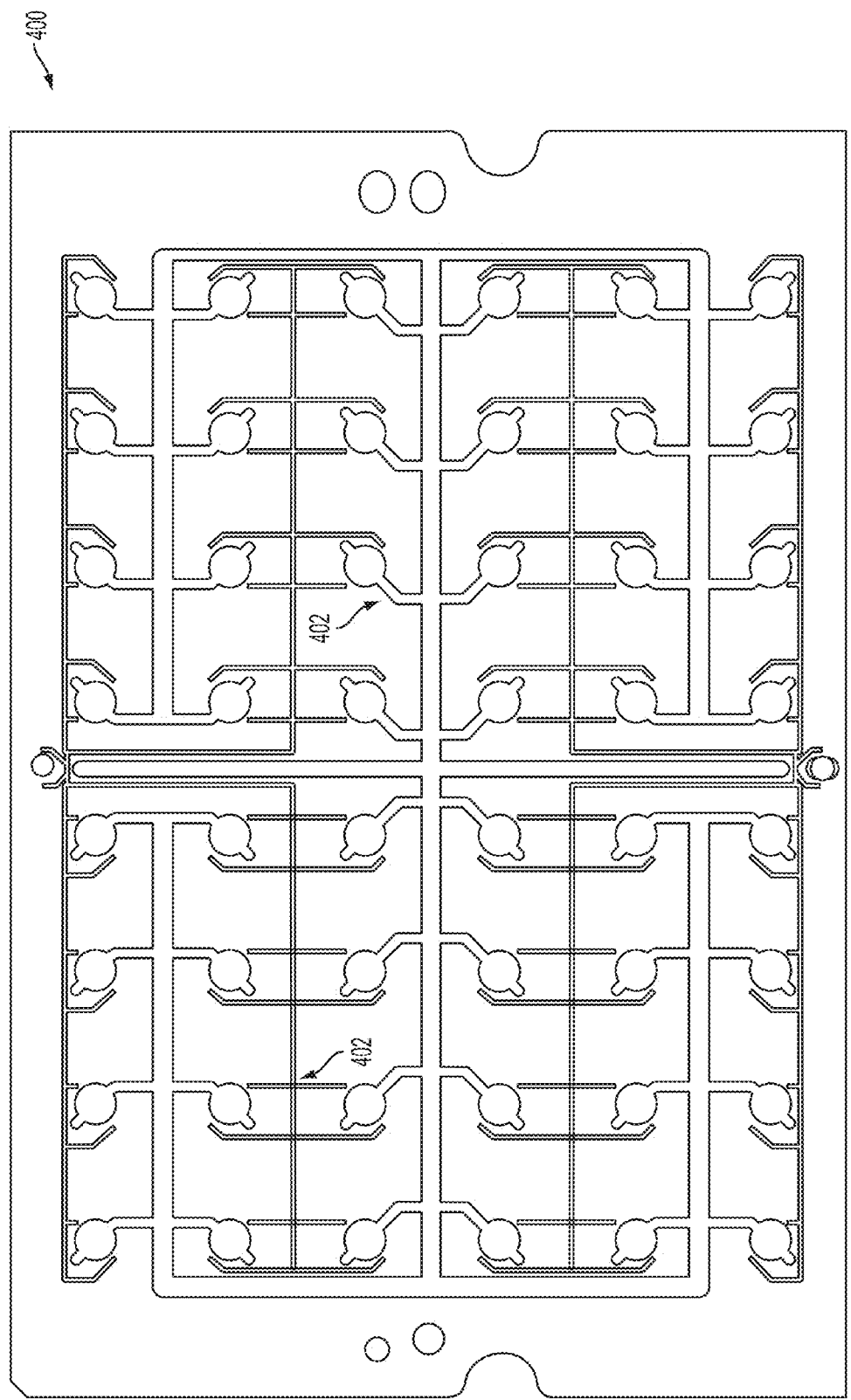
FIG. 4 depicts one exemplary implementation of a second layer of the monolithic microelectrode array plate.
Figure 5:
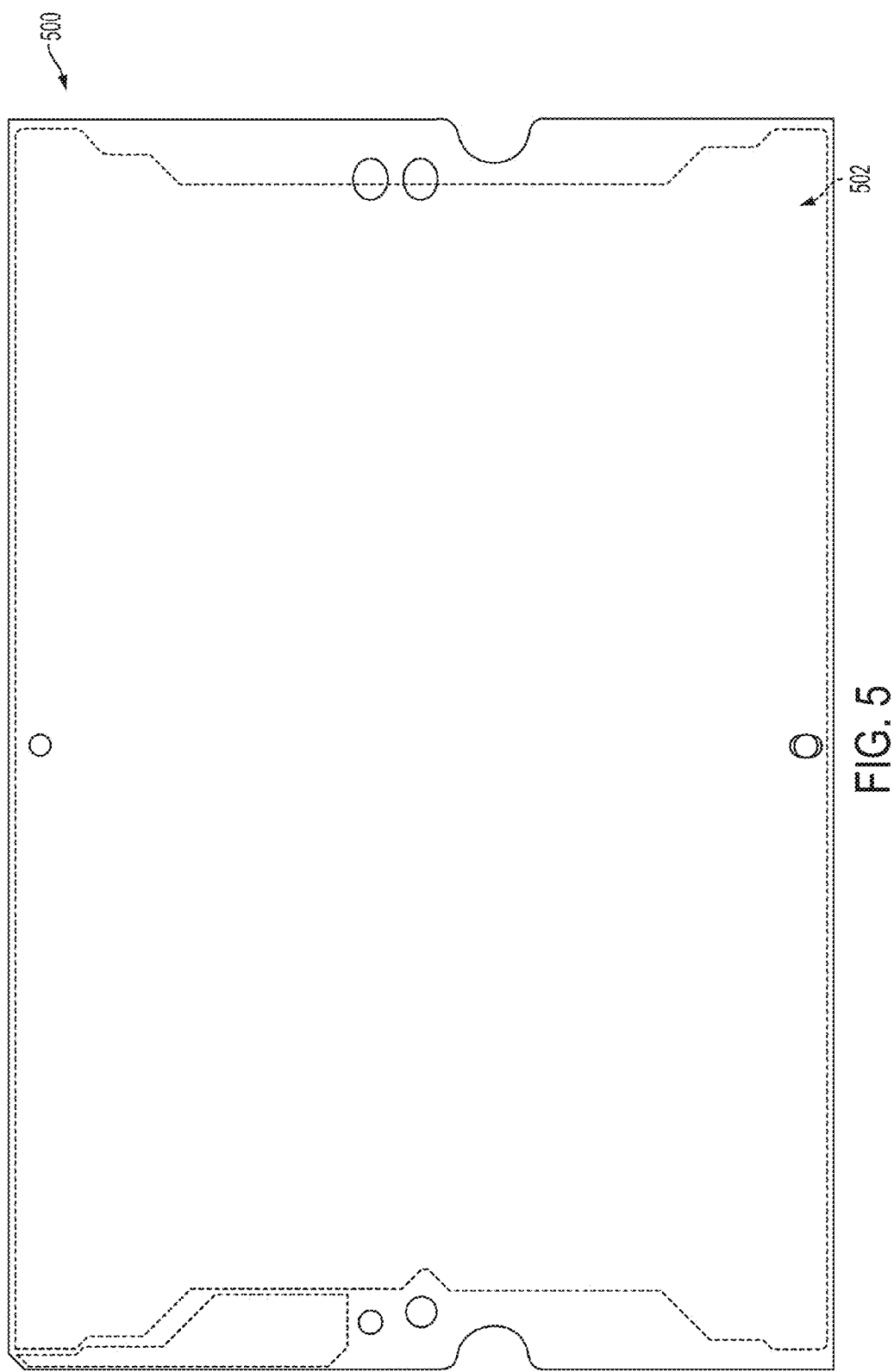
FIG. 5 depicts one exemplary implementation of a third layer of the monolithic microelectrode array plate.
Figure 6:
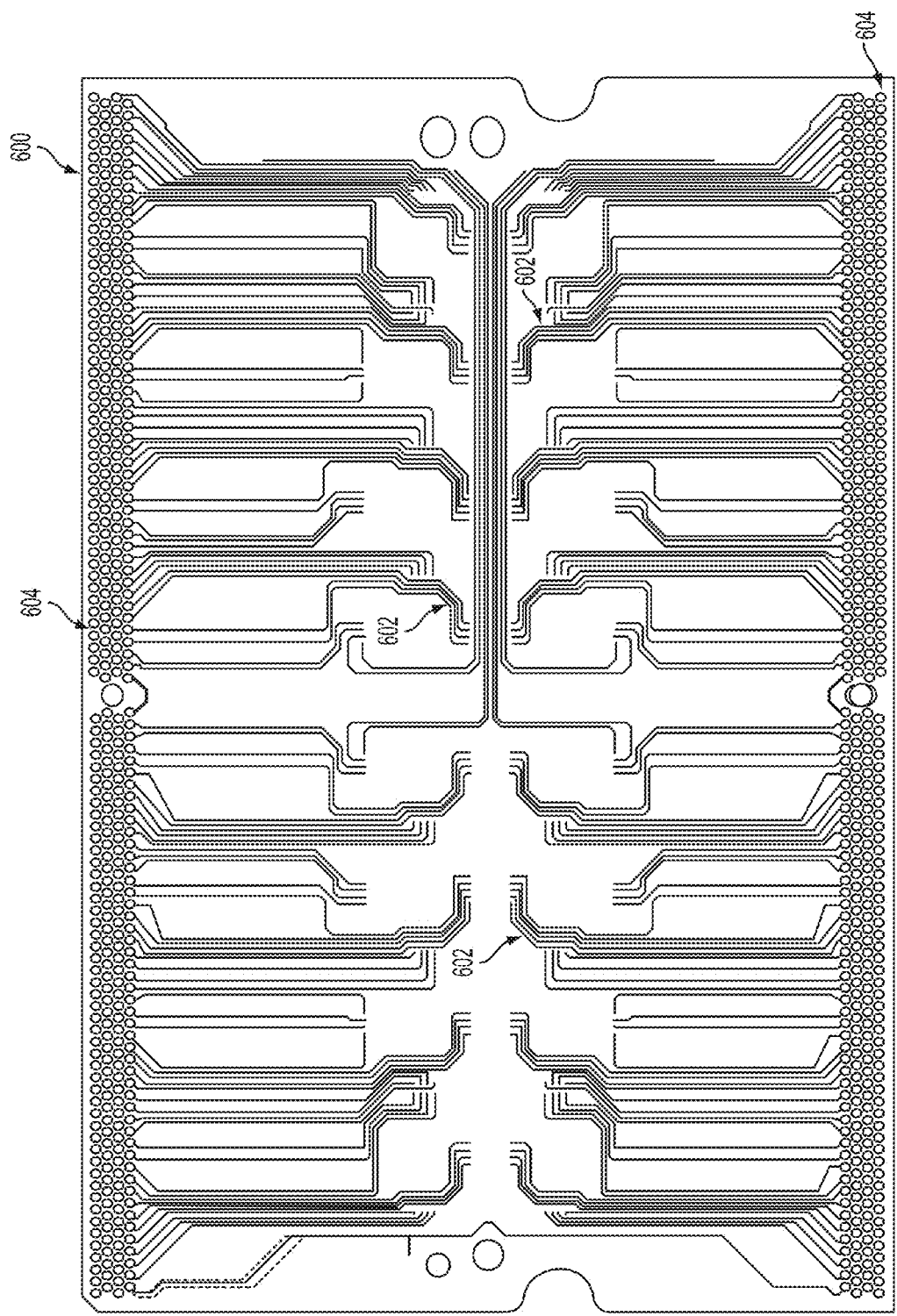
FIG. 6 depicts one exemplary implementation of a fourth layer of the monolithic microelectrode array plate.

For high-throughput electrophysiology, large-area, ANSI/SLAS-compliant microelectrode array (MEA) plates can be important as industry standard compliance can provide compatibility with other high-throughput instrumentation such as, for example and without limitation, plate readers, robotics handlers and the like. However, distributing hundreds-to-thousands of micro-scale sensors across a macro-area plate can present challenges within modern microfabrication and process/device design. The present disclosure describes devices, systems and methods to form an MEA-based electrophysiology culture plate having the following characteristics important to achieving an ANSI/SLAS-compliant, high-throughput MEA:

In one aspect shown in FIG. 2, the present disclosure can provide for high-throughput MEA culture well plates 102 that comprise an MEA plate 104 that can be fully vertically integrated with a culture well plate 106. In a further aspect, the monolithic MEA plate 104 and culture well plate 106 can be joined by an intermediate adhesive 116. In another aspect, the monolithic MEA plate can be monolithic, and, in additional or alternative aspects, can comprise, for example and without limitation, polymers, glass, glass-reinforced epoxy resin and the like.

MEA Plate

Figure 7:
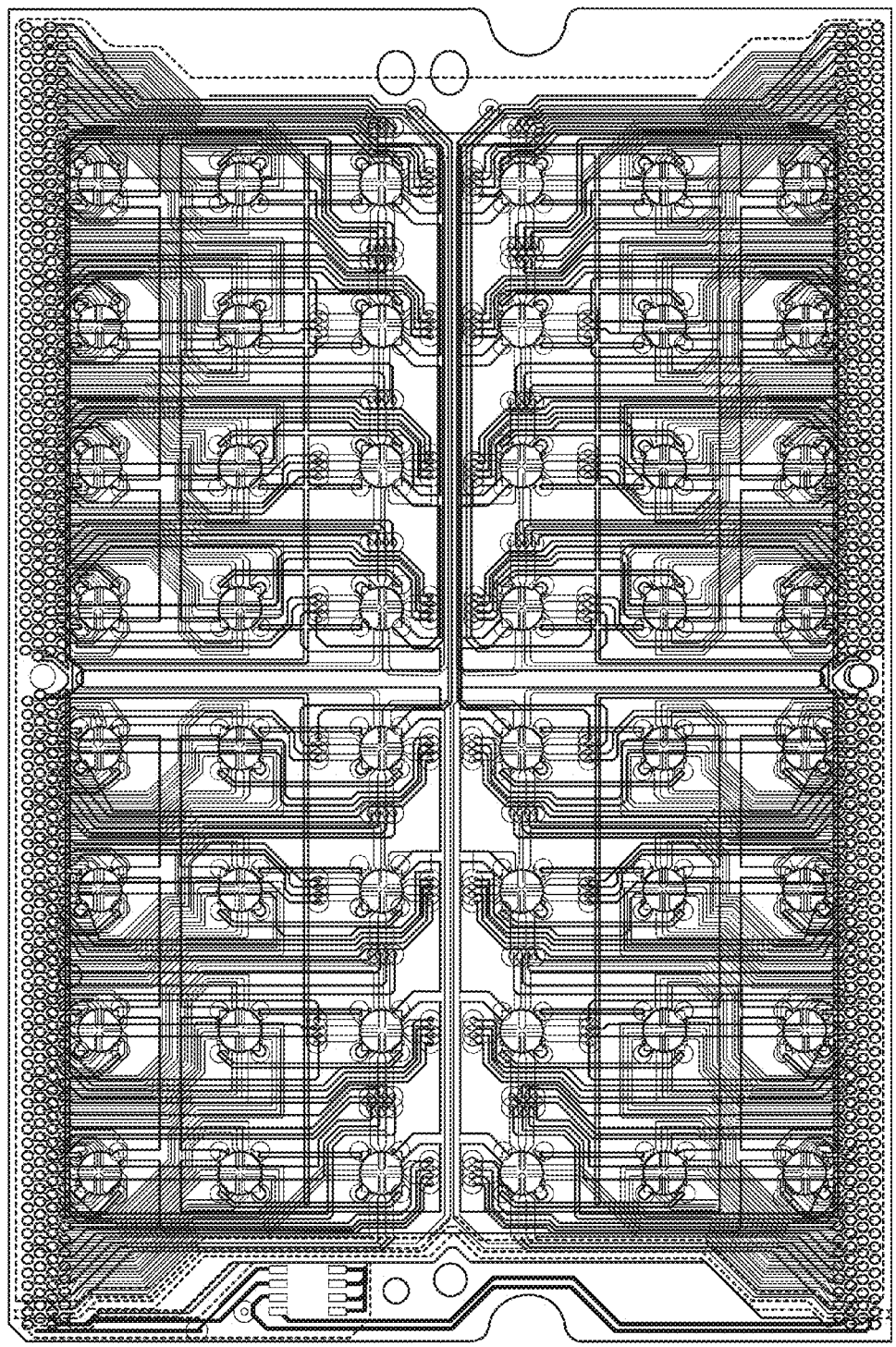
FIG. 7 depicts the first layer, second layer, third layer and fourth layers of the monolithic microelectrode array plate superimposed upon each other.
Figure 8:
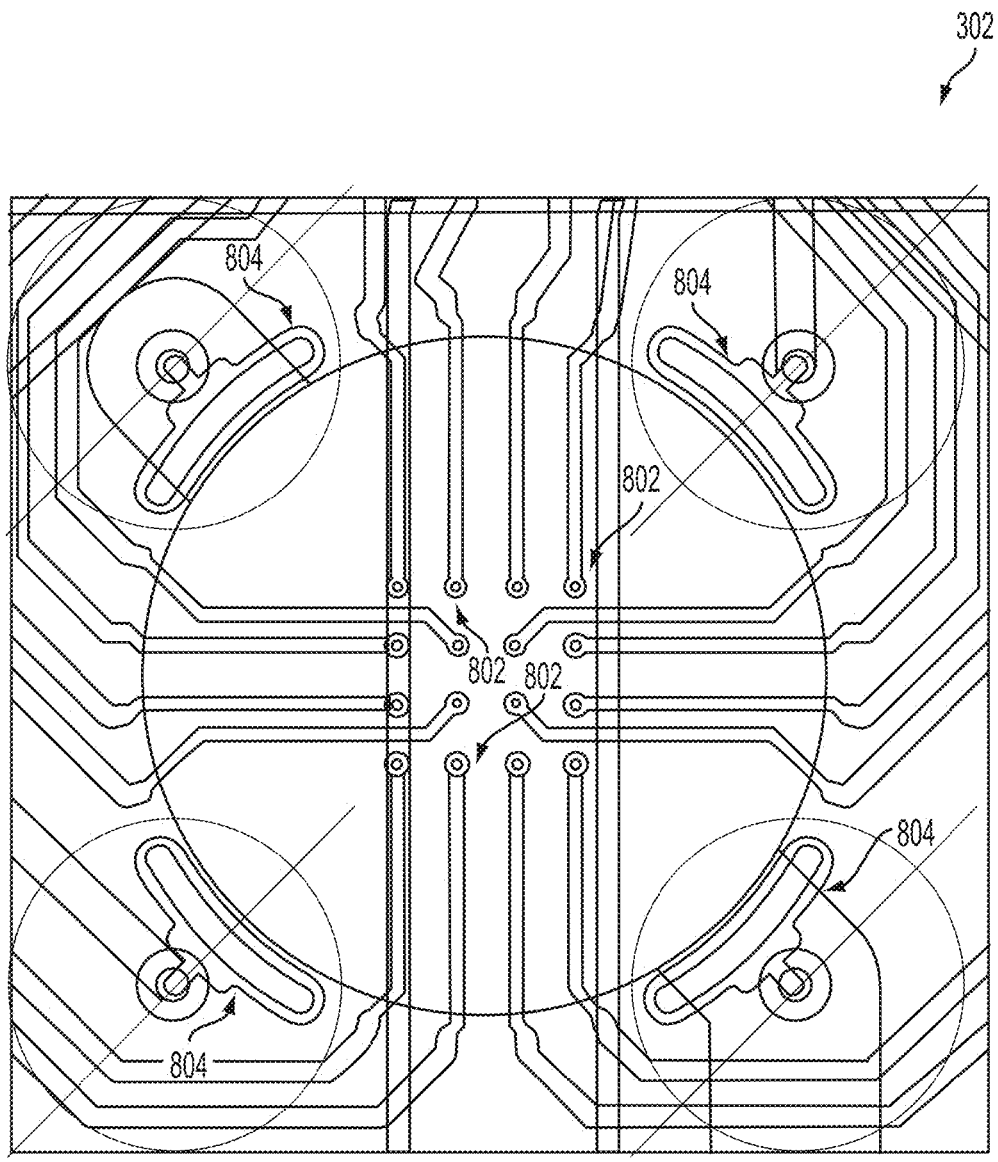
FIG. 8 depicts the underlying portion of a monolithic MEA plate in one implementation of a culture well plate having 48 wells.

One aspect of the present invention shown in FIGS. 3-8 comprises a monolithic MEA plate having a plurality of layers having electrodes, electrode routing and vias that ultimately provide for electrical communication between the culture well contents and the electronics unit. In one illustrative example, the monolithic MEA plate can comprise four layers where the first layer 300 comprises a plurality of MEA arrays 302 and a first microelectrode routing 304 patterned thereon, wherein each MEA array 302 comprises a plurality of reference electrodes 802 and a plurality of microelectrodes 804, a second layer 400 comprising reference electrode routing 402 in electrical contact with the plurality of reference electrodes 802, a third layer 500 comprising a ground plane 502 in electrical contact with the reference electrode routing 402, and a fourth layer 600 comprising a second microelectrode routing 602 in electrical contact with the first microelectrode routing 304 and a corresponding contact pad 604 formed on a lower major surface of the monolithic MEA plate. FIG. 7 illustrates the first layer 300, the second layer 400, the third layer 500 and the fourth layer 600 superimposed on each other. FIG. 8 depicts the underlying portion of a monolithic MEA plate in one implementation of a culture well plate having 48 wells.

In one aspect, the present disclosure can provide for bottom-side contact pads 504 within the footprint of the ANSI or SLAS prescribed dimensions of the MEA culture plate. In order to interface with industry-standard robotic handlers and instrumentation, the MEA culture plate can be configured such that no part of the contact pads extends beyond the ANSI or SLAS-prescribed footprint. Moreover, the contact pads can be located on the bottom of the MEA culture plate, so as to effectively preserve the topside for experimental preparation and execution.

In another aspect, the present disclosure can provide for high-density electrical contact pads on the periphery of the device. In specific embodiments where a multiplexing circuit cannot be embedded into the plate, high-density, bottom-side contact 504 pads can be positioned on the periphery of the device. Avoiding placing contact pads in the interior spaces facilitates optical transparency under the wells and/or the use of multiple well configurations with the same pad configuration.

Microfabrication of Opaque HTMEAs

In one aspect, one method to form an opaque monolithic MEA plate involves patterning approximately 50 μm metal traces and approximately 40 μm laser-patterned vias (or openings) on traditional PCB substrates such as, for example and without limitation, FR-4, polyimide, and liquid crystal polymer (LCP), and the like. Other polymer substrates such as, for example and without limitation, polyethylene naphthalate (PEN), polyethylene terephthalate (PET), other varieties of polyimides such as transparent polyimide, polyesters, polytetrafluoroethylene (PTFE) and the like can optionally be substituted for polyimides, e.g., Kapton. In an alternate or additional aspect, higher-end PCB technologies can enable much smaller features, e.g., lower than about 50 μm metal traces and about 40 μm laser-patterned vias.

In one aspect, in order to accommodate 768 stimulation/recording microelectrodes with additional integrated reference electrodes in a high-throughput ANSI/SLAS format, four layers of routing can be required to route all signals from the bottom side to the topside for microelectrode access. Contact pads for electronics access can be defined along the perimeter of the device. The definition of four rows of such pads ensures the ability to connect to all 768 electrodes on the device in a variety of configurations without affecting ANSI/SLAS standard micro-titer culture well locations (for 1, 6, 12, 24, 48, 96, 192 384, and higher well count culture well designs). The pads can be about 1000 μm by about 800 μm and can have a pitch of about 1200 μm. The shortest distance between the pads, however, can be about 320 μm. The entire metal track routing in this design can be performed with about 3 mil (or about 75 μm) metal track width with about 3 mil spacing in the microelectrode area (illustrated in FIG. 8) and about 5 mil (or about 125 μm) metal track width with about 5 mil spacing elsewhere, thereby ensuring cost-effective production.

In one aspect of the present disclosure, the five basic PCB processes used to form the MEA plate can comprise a combination of photoengraving, milling, etching, plating and lamination. In light of the present disclosure, one skilled in the art will appreciate that PCB processes are typically performed on large area substrates (e.g., panels that can be 19-inch by 14-inch or larger) and outside the cleanroom. Accordingly, PCB processes tend to be more cost-effective than microfabrication/microelectronic processes, however they produce larger feature sizes as compared to microfabrication processes. With the repetition of the five basic processes above, complex devices can be created both on flexible and flex-rigid substrates.

Figure 9:
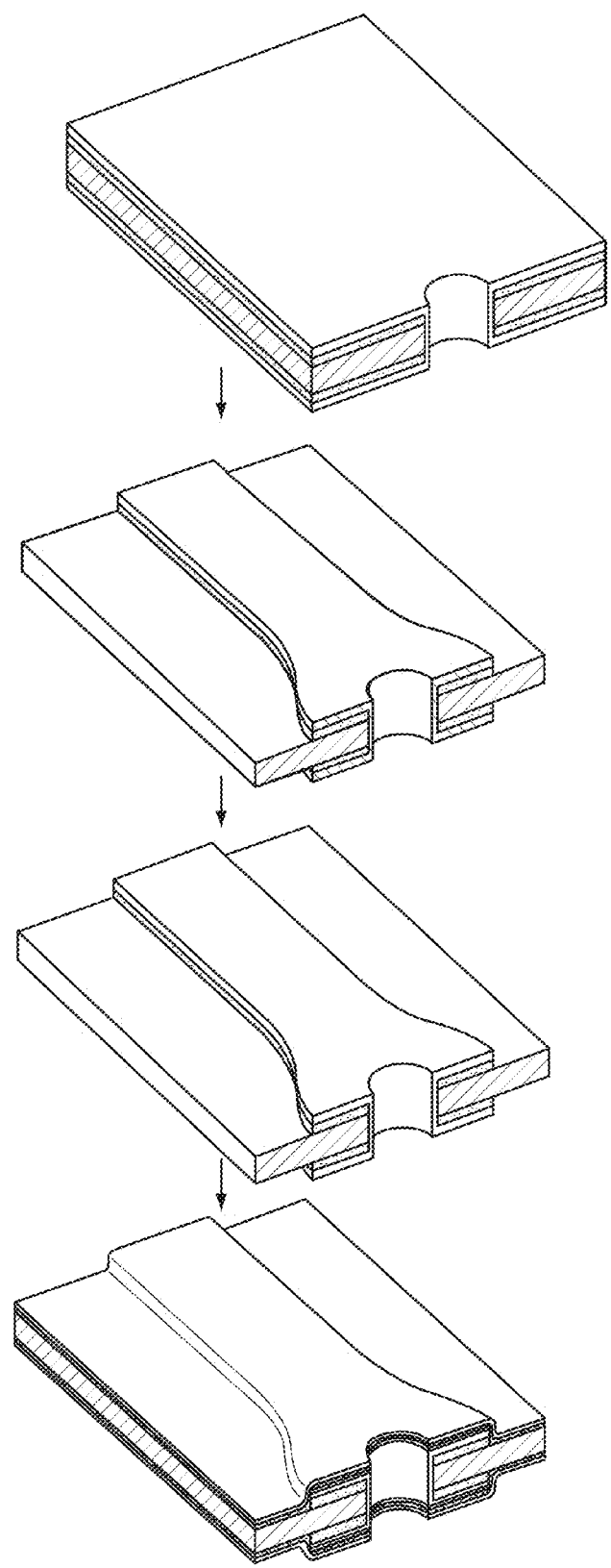
FIG. 9 illustrates one exemplary process flow schematic for defining the electrical routing and contact pats on one implementation of a PCB substrate.

In one aspect of the present disclosure shown in FIG. 9, photoengraving can be used to define the routing traces and contact pads on a flexible or a flex-rigid substrate. Typical PCB substrates such as, for example and without limitation, FR-4, Kapton, LCP and the like, can have copper layers of various thicknesses (specified typically by weight of copper in ounces) glued or electroplated on them. Subsequently, a dry film mask can be coated on the copper-plated PCB and imaging can be performed using a UV lamp to define the routing features. Then, the dry film resist can be developed and the board can be etched to remove copper from unwanted areas. One skilled in the art will appreciate that the copper layer can be adhered to both sides of the PCB substrate and double-side processing can be performed so that both sides can be electrically connected using the other standard processes discussed herein.

In another aspect of the present invention, milling, drilling and the like can be used to create vias or through-holes using standard mechanical drill bits for larger vias or laser machining for smaller sized vias. One skilled in the art will appreciate that laser machined vias have the added advantage of highly controllable drill depth.

In another aspect of the present invention, both electroless plating and electroplating of copper or other metals can be performed in standard PCB processing. Electroless plating can be used to provide a seed layer or adhesion layer for subsequent electroplating. For example and without limitation, nickel can be used to create a seed layer having nanometer-scale thickness. In another aspect, electrical contact between the routing layers of the PCB can be provided through electroplated copper vias.

In light of the present disclosure, one skilled in the art will appreciate that, by utilizing a sequence of the five basic PCB procedures, four routing layers can be fabricated and combined together into a monolithic device using intermediate insulating layers through lamination processes.

In another aspect, before the top metal layer can be laminated, a soft gold layer can be electrodeposited on the copper. In certain aspects, the gold layer electroplating can be important in the definition of the final microelectrodes. In a further aspect, the soft gold layer can be defined to achieve sufficient thickness, e.g., about 20 to about 30 micro-inches or about 0.5 to about 0.762 μm) to withstand laser micromachining that is performed at a later stage. In one example, a sufficient thickness can be from about 20 to about 30 micro-inches. In light of the present disclosure, one skilled in the art will appreciate that such thicknesses of electroplated metal on thin film metal can be sufficient to withstand the removal of polymer materials deposited on top of the electroplated layer utilizing laser micromachining. In a further aspect, following gold plating, a layer of Kapton can be laminated on top of the finished 4-layer rigid FR-4 with all the microelectrodes defined and routed. In one example, the Kapton layer can be 12.5 μm thick with 12.5 μm acrylic adhesive.

Figure 10:
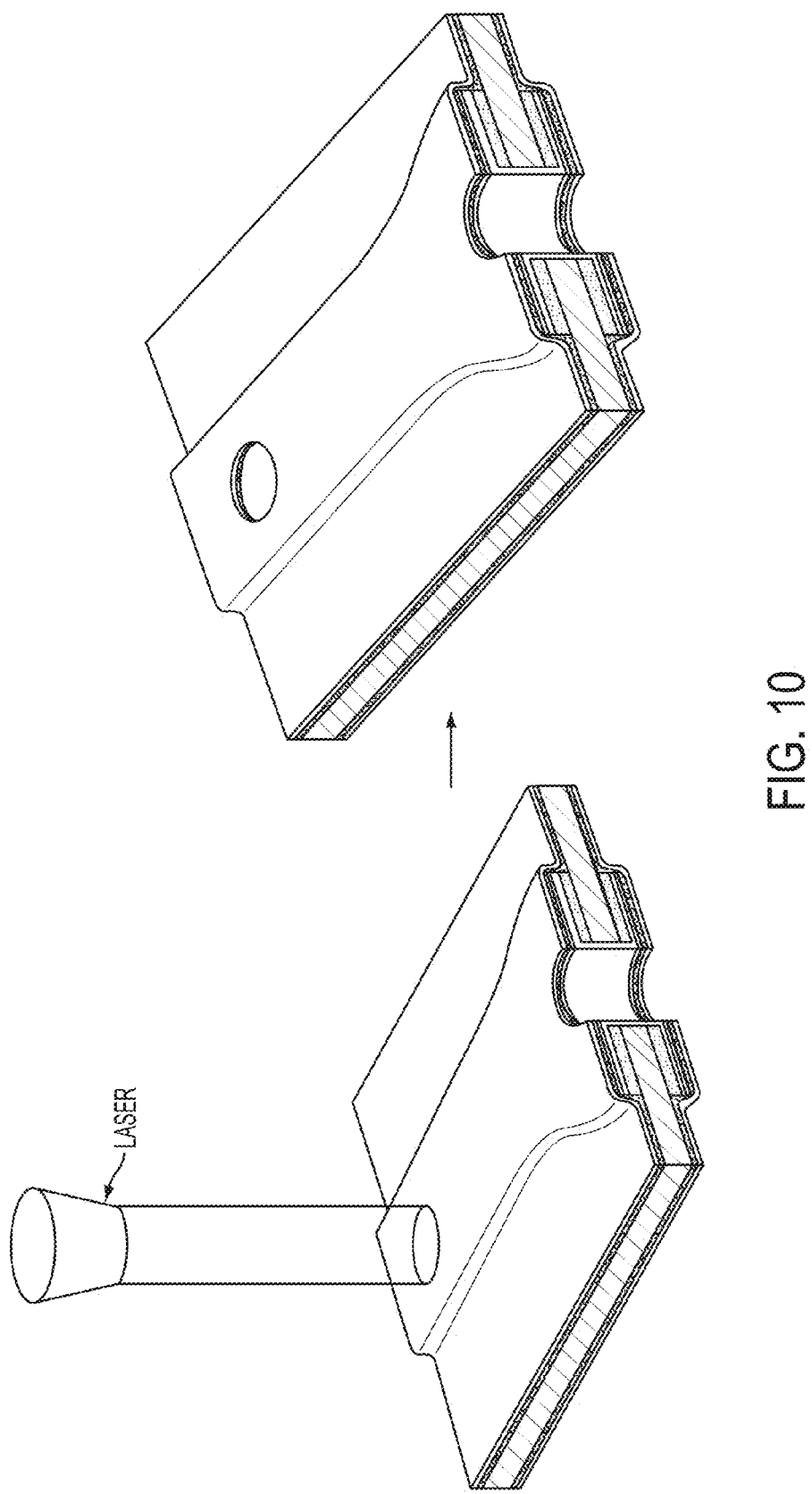
FIG. 10 illustrates one exemplary process flow schematic for defining the electrodes.
Figure 13B:
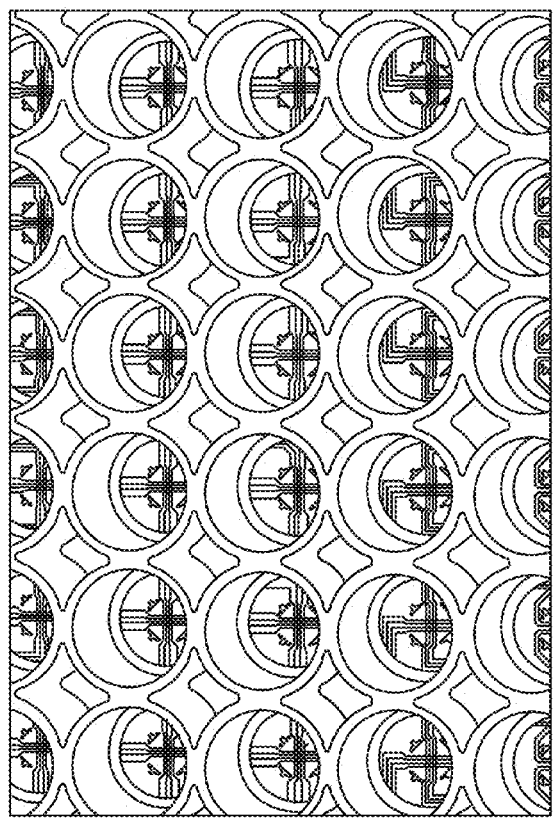
FIG. 13B shows an enlarged view of the optical micrograph of the assembled 48-well of FIG. 13A.
Figure 13A:
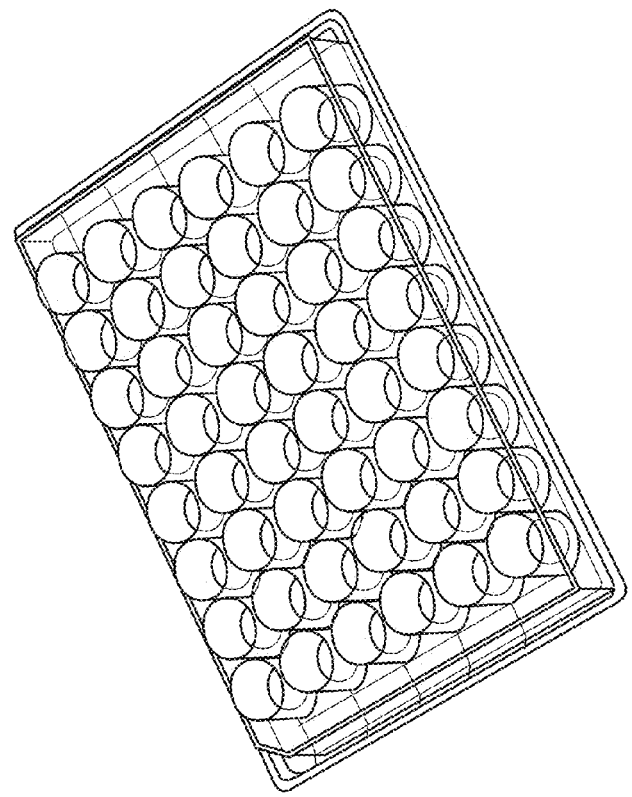
FIG. 13A shows a perspective view of one aspect of an optical micrograph of an assembled 48-well MEA fabricated on an opaque panel.

Subsequently, in another aspect depicted in FIG. 10, the Kapton can be selectively laser micromachined utilizing either a $CO_2$ or a UV laser to define the microelectrodes. One skilled in the art will appreciate that an excimer laser system operating at about 248 nm can be well suited for micromachining polymers. Laser/material interactions during ablation can be complex and depend both on the laser characteristics such as, for example and without limitation, wavelength, pulse duration, intensity and material characteristics such as, for example and without limitation, absorption spectra, ease of evaporation and the like. In a further aspect, the amount of material removed can be related to a threshold defined by the properties of the material being micromachined. In yet another aspect, laser micromachining processes can deposit carbon residue on the parts, therefore plasma and solvent cleaning processes can be used to remove this residue and to complete a monolithic 48-well opaque MEA board. FIG. 13 illustrates an optical micrograph of an assembled 48-well MEA fabricated on an opaque panel.

Figure 11B:
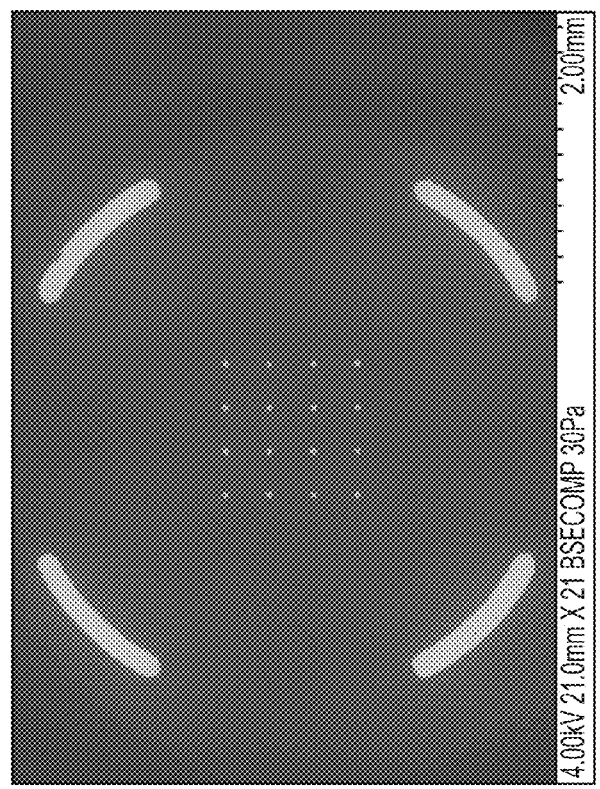
FIG. 11B shows an SEM micrograph of one implementation of a nanotextured gold electrode.
Figure 11A:
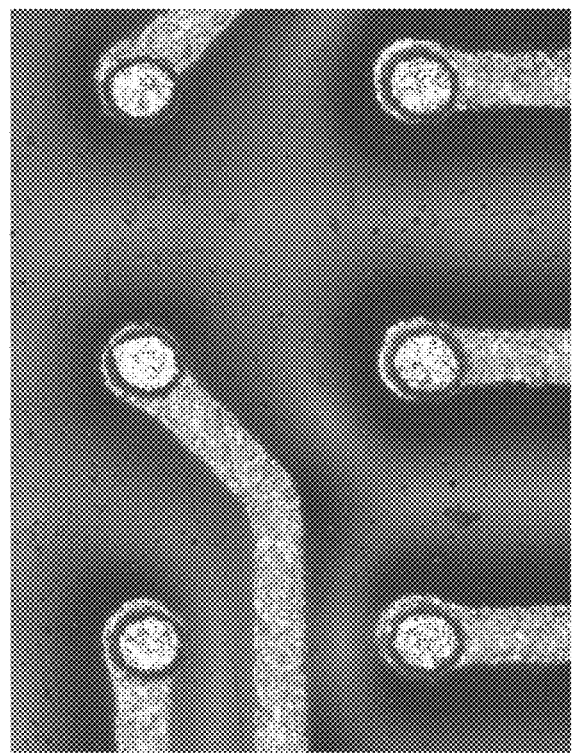
FIG. 11A shows an optical micrograph of one implementation of a nanotextured gold electrode.

As shown in FIGS. 11A and 11B, it is another aspect of the present disclosure that the electrode characteristics can be defined by soft gold electroplating and laser micromachining processes. Both of these processes can define a gold layer that can be textured on a nano-scale, e.g., 100 s of nanometers. In light of the present disclosure, one skilled in the art will appreciate that texturing leads to an increased surface area and, thus to superior impedance performance compared to thin film process-based MEA plates.

Microfabrication of Transparent HTMEAs

Traditional microfabrication can be typically performed on substrates such as silicon and glass. MEA plates for in vitro and in vivo applications have been demonstrated on these substrates since the late 1960s. More recently such MEA plates have been developed on a variety of polymers such as, for example and without limitation, parylene, Kapton, poly dimethyl siloxane (PDMS), SU-8, poly methyl methacrylate (PMMA), polyurethanes (PU) and the like. One skilled in the art will appreciate that microfabrication affords advantages such as, for example and without limitation, scalability, nanoscale feature sizes, robust manufacturability, CMOS integration (on silicon substrates only), advanced processing tool set, yield optimization for high-volume production and the like. However, as discussed previously, MEA plates can require relatively large-area compatible definition of micro- and nano-scale features and hence some of the traditional advantages of wafer-based microfabrication processes can be lost. Additionally silicon cannot be used due to transparency requirements. One skilled in the art will appreciate that glass panel microfabrication, made popular and cost-effective by the display, flexible electronics and solar cells industries, is particularly well suited for the manufacture of MEA plates.

Figure 12:
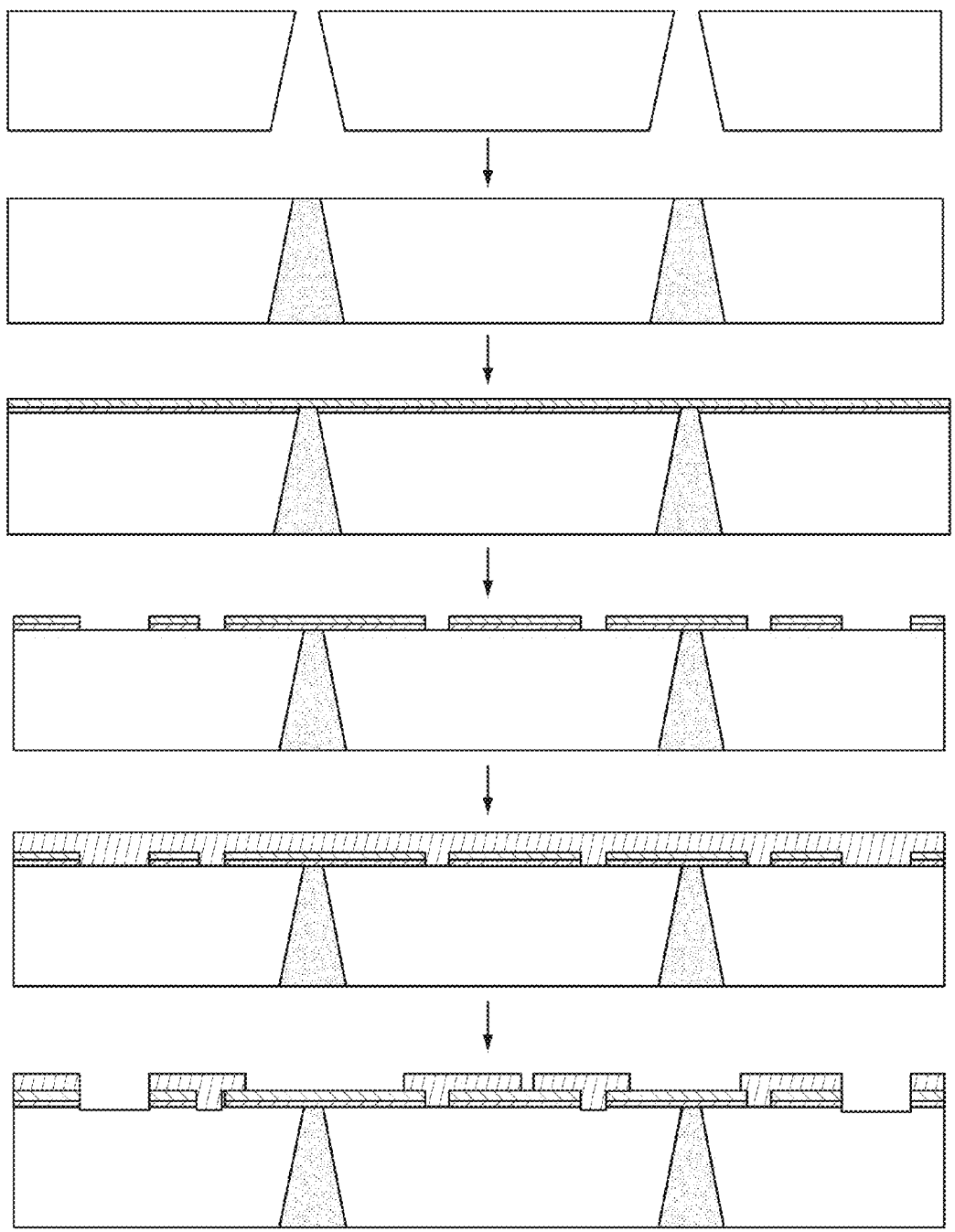
FIG. 12 illustrates one exemplary process flow for monolithic microelectrode array fabrication on a glass substrate.

In another aspect of the invention shown in FIG. 12, the present invention provides for a process flow for MEA plate fabrication on a glass panel. In light of the present disclosure, one skilled in the art will appreciate that, with minor modifications in processing steps these glass panels can be substituted by polymer panels. Polymers such as, for example and without limitation, polycarbonate (PC), polystyrene (PS), poly methyl methacrylate (PMMA), cyclic olefin co-polymers (COCs) and the like can be ideal candidates for such a process but careful consideration needs to be paid to the processing temperatures, mechanical (e.g., roughness) and optical (e.g., transparency) properties of such polymers before they can be applied to transparent HTMEAs.

In one aspect of the present disclosure, vias can be created in the glass panel. In an illustrative example, the thickness of the glass can be about 1 mm. Established technologies such as, for example and without limitation, powder blasting, high precision CNC milling and laser micromachining can be used to create the vias on the periphery of the substrate.

In a further aspect, the microfluidic vias and channels in a glass substrate can be formed by powder blasting. One skilled in the art will appreciate that powder blasting can be a flexible, cost-effective and accurate in the present application. Powder blasting utilizes photolithography to define the location of the vias and, subsequently, the exposed glass panel areas can be subjected to a powder that etches glass in those locations. The photoresist-covered areas deflect the powder such that there can be no etching in these areas. Feature size accuracy of approximately 25 μm can be achieved with powder blasting with minimal roughness (less than 2.5 μm) imparted to the vias.

In another aspect, high precision CNC milling can be utilized to microfabricate vias on glass panels. CNC milling can accurately machine glass over large areas. In one illustrative example, CNC milling can achieve about 5 μm placement accuracy over relatively large areas such as, for example and without limitation, several hundred millimeters.

In another aspect, vias on glass substrates can be created using laser micromachining One skilled in the art will appreciate that materials used to fabricate the MEA plate will affect the type of laser best suited for this function. As one illustrative example, a $CO_2$ laser is suitable for micromachining certain varieties of glass, such as, for example and without limitation, fused silica and the like.

In another aspect, the vias previously formed can be subjected to electroplating, screenprinting or the like in order to establish a conductive path through the via. In light of the present disclosure, one skilled in the art will appreciate that screenprinting can be particularly well suited to form the vias since it can be large area processing compatible technique and has the ability to produce fine features with excellent accuracy. Screenprinting comprises a process of utilizing a highly intricate mesh through which a conductive adhesive can be deposited in a predetermined pattern defined on the mesh. In one aspect, the level of intricacy of the mesh can depend on the size of the vias or traces to be defined. Subsequently, conductive epoxy deposition can be performed utilizing a squeegee which makes intimate contact with the screen and whose motion can be accurately controlled. Parameters such as the force and speed can be optimized to produce the pattern of the filled conductive vias. Additionally vacuum might be required to ensure complete filling of the tallest vias. In one exemplary aspect, the tallest vias can be about 1 mm tall.

In another aspect, the screen printed substrate can be polished to achieve a substrate with minimal surface roughness for further processing.

In further aspects, the screen printed glass panel can undergo additional processing that can involve structuring the metal tracks, insulation and microelectrodes. One skilled in the art can appreciate that standard microfabrication technologies which are well established in mass micro-manufacturing such as, for example and without limitation, lift-off and deposit/etch can be utilized to define the metal tracks on the screen printed glass panel.

In other aspects, regions of insulation can be selectively defined on the current form of the glass panel. In one illustrative example, SU-8 insulation can be defined using a photolithography process. In another illustrative example, silicon dioxide or silicon nitride insulation can be defined utilizing a PECVD process, followed by a photolithography process and an etch process. Here, the etch process (i.e., wet or dry etch or a combination of both) can define the recording sites/microelectrodes while the photoresist protects the rest of the device from etching. In yet another example, parylene can also be defined utilizing the process described for silicon dioxide and silicon nitride. The deposition of parylene however can be a room temperature vapor deposition.

In another aspect, microelectrodes can be formed on individualized devices obtained by dicing the glass panel into individual units utilizing a large area finesse electroplating process at the assembled device level. In one further aspect, the microelectrodes can be formed from nano-porous platinum.

Culture Plate

In one aspect of the present disclosure, a multi-well biologic culture plate configured to be joined to the MEA plate can be provided. In another aspect, the biologic culture plate can further comprise a lid. The biologic culture plate and lid can be formed, for example and without limitation, by conventional injection molding techniques. In a further aspect, the biologic culture plate and lid can comprise materials such as, for example and without limitation, polystyrene, polycarbonate and the like.

In another aspect, the biologic culture plate is configured to be ANSI/SLAS compliant.

In another aspect, the lid comprises a double baffled edge, to reduce the amount of fluid lost through evaporation and/or maintain sterility.

In another aspect, at least one electronics pocket can be formed on the biologic culture plate to allow space for IC and sensor placement. In light of the present disclosure, one skilled in the art will appreciate that either the flex-PCB technology or glass panel microfabrication technology used to create the MEA plate can be well suited for adding sensors and ICs. In one illustrative example, a 48-well electrophysiology culture plate comprises an EEPROM memory chip disposed on the MEA plate and within in a pocket formed on the biologic culture plate. It is a further aspect of the present disclosure that the chip can be used by the electronic data acquisition system to store information about the electrophysiology culture plate such as, but not limited to, the type of plate, electrode mapping, specific electrode properties and the like. In an additional or alternative aspect, the chip can be used to store user information about the experiment being performed such as, for example and without limitation, when the experiment started, the types of cells cultured or the compounds, concentrations applied, and the like. In other aspects, the electronics pockets can also be used for other types of IC chips such as, for example and without limitation, temperature sensors, $CO_2$ sensors, humidity sensors, pH sensors, $O_2$ sensors and the like.

In other aspects, the present disclosure can provide for electrophysiology culture plates that can be sterilized using simple treatments to eliminate the risk of cytotoxicity and do not require surface preparation (apart from standard biomolecular treatments) for cell culture applications.

Figure 21:
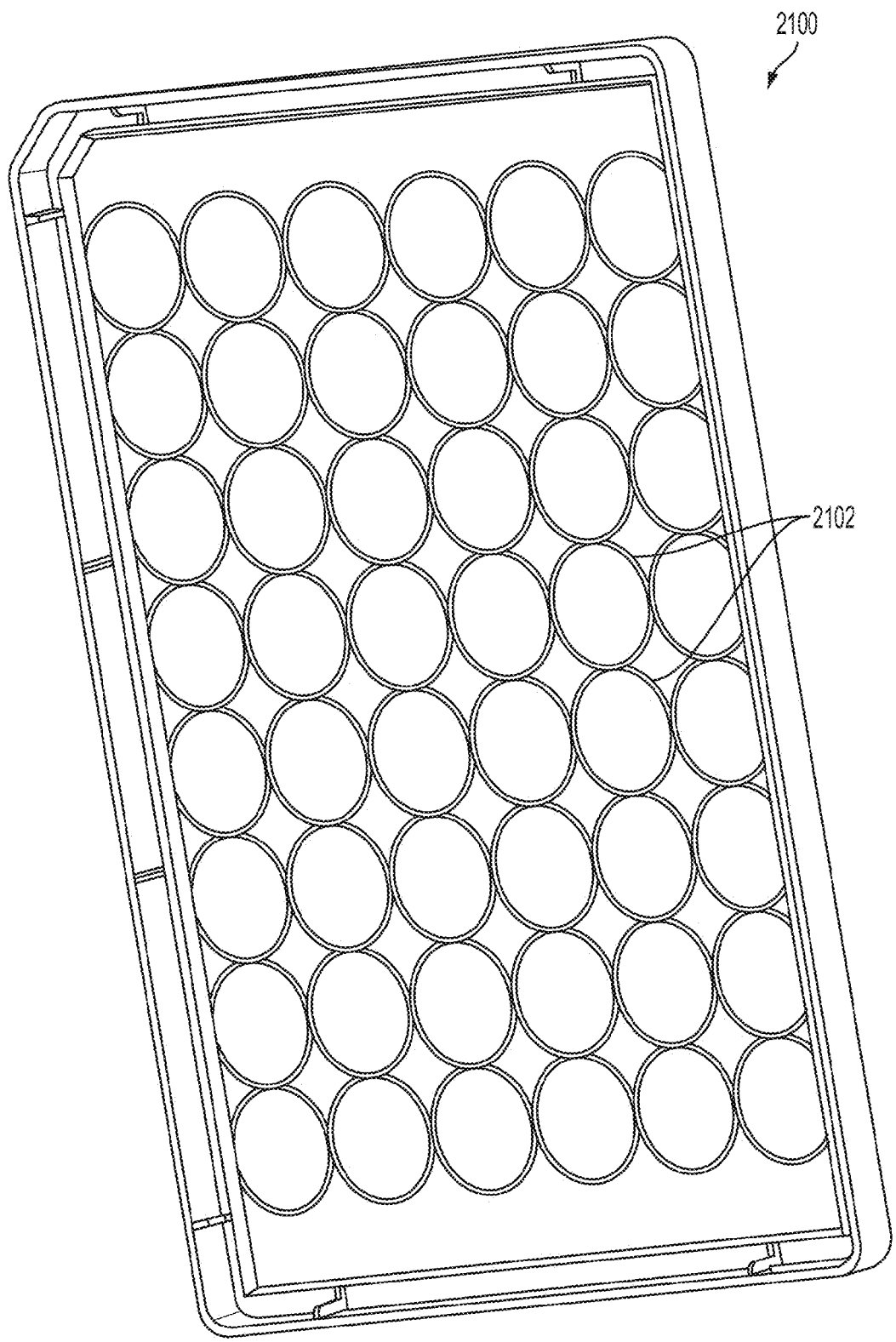
FIG. 21 shows a perspective view of one aspect of a culture well plate lid.

In other aspects, the present disclosure provides for a culture well plate configuration: operable to prevent communication or contamination between adjacent wells. In a further aspect shown in FIG. 21, the lid 2100 comprises a plurality of well caps 2102 configured to overlie each of the culture wells. In another aspect, each of the plurality of culture wells has the same height relative to the peripheral wall of the culture plate.

Figure 20B:
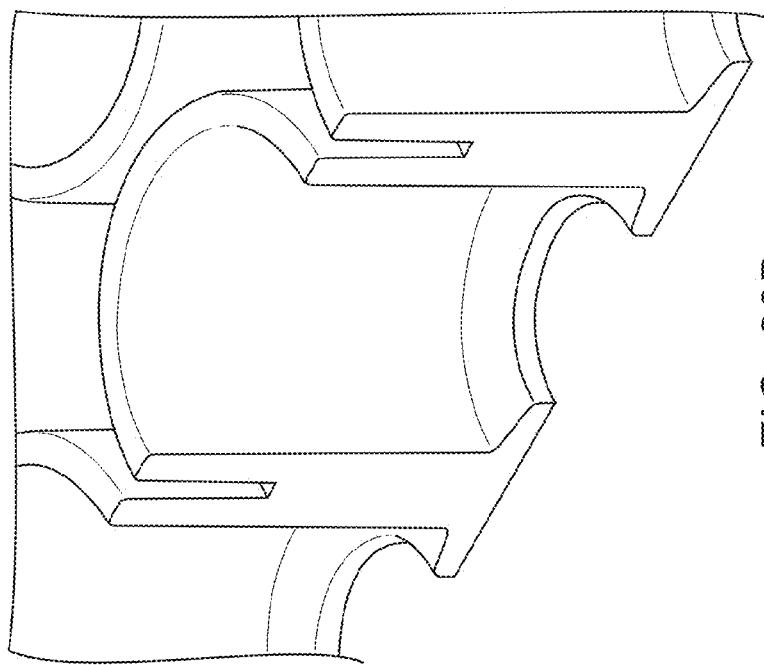
FIG. 20B is a perspective view of the culture well shown in FIG. 20A.
Figure 20A:
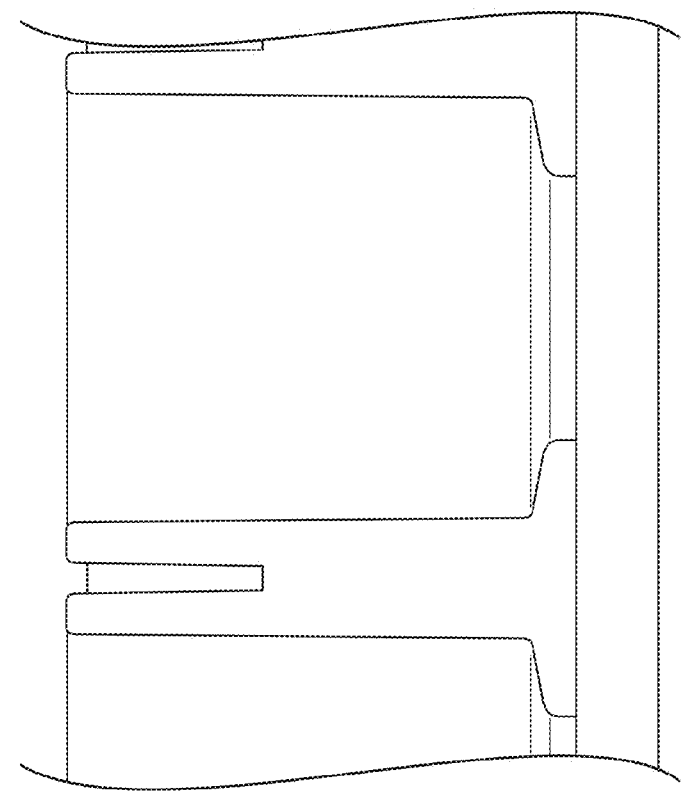
FIG. 20A is a cross sectional view of one aspect of a culture well having a smaller footprint at the bottom of the well as compared to the top of the well.

In other aspects shown in FIGS. 20A and 20B, the present disclosure provides for culture well plates having culture wells configured to concentrate the volume of the cells/biomolecular treatments deposited specifically on the microelectrode area. In yet other aspects, the present disclosure provides for culture well plates having culture wells comprising an upper diameter and a lower diameter, wherein the upper diameter is greater than the lower diameter. In a further aspect, each culture well can circumscribe either a conical or frustoconical structure on a lower portion of the well.

In another aspect shown in FIGS. 17A-19, the biologic culture plate and MEA plate contain at least one alignment feature 1701 configured to define the directionality of the plate or align the high-throughput culture well plate to a die-cut adhesive and the electrode substrate or both. In another aspect, once assembled, a keying feature 1702 can align the electrophysiology culture plate assembly to the docking mechanism and the high-density connectors located in the electronics unit.

Assembly and Packaging

In one aspect, the final assembly of the electrophysiology culture plate can be performed in a scalable fashion. Here, all of the steps of assembly can accommodate assembly of large numbers of devices simultaneously. As shown in FIG. 2, there are at least three components to join together: the 48-well MEA plate, a die-cut or laser-cut adhesive and a biologic culture plate. In one illustrative example, the assembly process can be performed on a 3.5 inch×5 inch fixture configured to assemble one device at a time. In a further aspect, the fixture can be configured to accommodate a plurality of devices. In a further example, the fixture can comprise at least 12 inch×18 inch panels. In another aspect, the adhesive can be precisely aligned under a stereomicroscope with an accuracy of approximately 100 μm with the MEA plate and biologic culture plate in multiple steps of a vacuum-assisted compression bonding process. In an alternate aspect, compression can be applied to the nearly-final electrophysiology culture plate utilizing a lamination press or a standard compression press.

Electronics Unit

Figure 22:
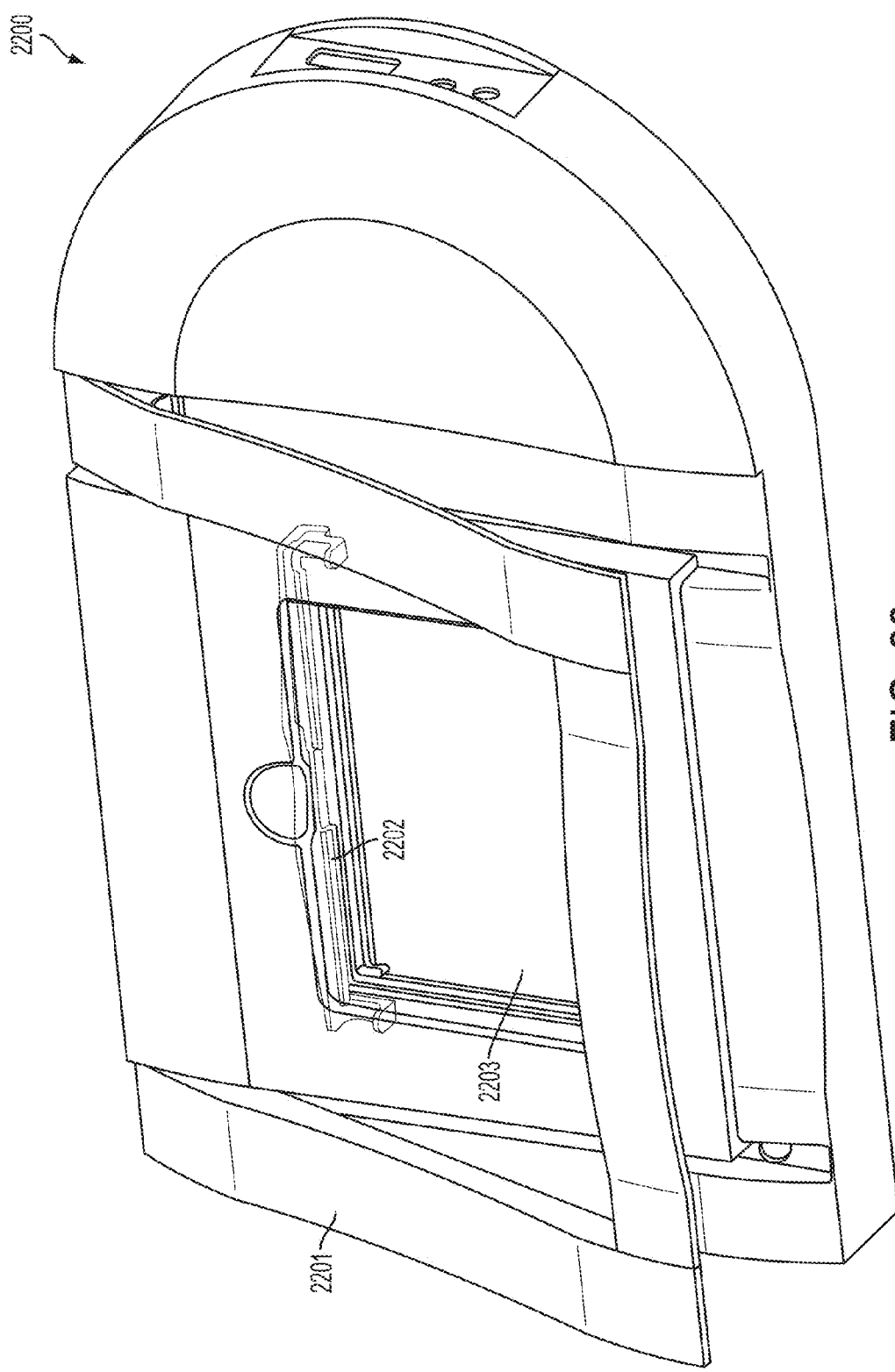
FIG. 22 depicts one aspect of a clamping mechanism for clamping a MEA culture well plate.

In other aspects shown in FIGS. 22-23, the present disclosure can provide for an electronics unit 2200 coupled to microelectrodes that can be configured to stimulate the cell and record data therefrom, optionally, immediately thereafter. As one skilled in the art will appreciate, stimulation and recording immediately post-stimulation can be complicated and is not readily available in current commercial MEA systems because of the very different scales that stimulation and recording occur on. In the specific case of neural tissues, hundreds of millivolts are required to achieve a response due to stimulation through extracellular electrodes, while the same electrodes will show signals in the tens of microvolts when the tissue or cell culture generates a signal. Thus, four orders of magnitude of disparity exist between the stimulation and recording signal and effects of this disparity on the electrode renders signal recovery futile unless a recovery technique is used. This interference, commonly referred to as an artifact, includes the saturation of the signal amplifying elements and its effects in the signal processing chain during the recovery from these strong signals.

One aspect of the present disclosure provides for an electronics unit that employs closed loop artifact suppression that can incorporate feedback in the form of discharge amplifiers to quickly return the electrode to a useful range, compensating for effects that traditional, open loop systems do not. In one aspect, artifact suppression can be implemented by an ASIC configured to significantly reduce or eliminate the stimulation artifact. Here, the ASIC can include an electrode interface, a path for stimulating the electrode, preamplifiers with built in gain and bandwidth control, as well as multiplexing and output buffering. This custom design allows us to implement stimulation, artifact elimination, and recording on all 768 channels, which would not be possible using commercial off the shelf parts. Such an electronics unit is described in U.S. patent application Ser. No. 11/511,794 filed on Aug. 29, 2006, the contents of which are hereby incorporated by reference.

Alignment Features

In another aspect, the present disclosure can provide for at least one alignment feature integrated into the electrophysiology culture well plate. In a further aspect, high-density electrical contacts can be configured to align to the electronic systems configured to impart functionality to the microelectrodes.

In another aspect, the present disclosure can provide for non-restrictive electromechanical interfacing. More particularly, in order to accommodate automated liquid handlers as well as experiments in which evaporation control is utilized, the present disclosure can allow for addition or removal of the culture plate lid before or after attachment of the apparatus to the electronics unit.

In other aspects, the present disclosure provides for electrophysiology culture plates and an associated electronics unit having at least one pair of mating mechanical features to enable self-alignment between the electrophysiology culture plate and the high-density connectors associated with the electronics unit. In yet other aspects, the present disclosure also provides for electrophysiology culture well plates having at least one pair of mating mechanical features configured to facilitate alignment and attachment of the electrophysiology culture plate in the electronic unit.

System Mechanics Features

In one aspect, vertical system integration within the SLAS footprint can be achieved using high-density connectors within the electronic data acquisition system configured to interface with the electrophysiology culture plate through contact pads located on the bottom side of the electrophysiology culture plate around at least a portion of a perimeter region. In one aspect, such a system of high-density connectors does not require a connector on the MEA plate, thereby reducing the amount of space devoted to the connection interface. Such an interface can be implemented through a pattern of contact pads that can be fabricated through the standard flex-PCB processes or glass panel microfabrication processes, described above. In one aspect, the pins can be located around the perimeter of the plate, and, in further aspects, the pins can be located solely along the long sides in order to reduce interference with the culture wells. In light of the present disclosure, one skilled in the art will appreciate that such placement can be especially important for transparent substrates, where internal or backside traces and pads within the well boundaries would interfere with optical imaging. Additionally, the perimeter location of the pins and corresponding contact pads can enable flexible well (e.g., 1-, 6-, 12-, 24-, 48-, 96-, 384 and higher well count electrophysiology culture plates) and electrode configurations without requiring changes such as, for example and without limitation, hardware, docking or connectivity changes. In other aspects, the location of the contact pads in the perimeter region can also clear the backside for heater implementation. In one aspect, a heater can either be implemented in the electrode substrate PCB or be an external heater 2203 located beneath the electrophysiology culture plate and configured to transfer heat to the culture wells through direct contact.

In another aspect, the perimeter contact pads can enable a docking mechanism 2201 that can provide sufficient pressure to consistently engage the pogo-pins, without preventing topside access to the culture wells. The plastic high-throughput electrophysiology culture plate design includes a reinforced bottom edge protrusion used to dock the plate in place. The MEA system uses a mechanism 2202 that grasps this plate protrusion and applies force directly to these edges. This prevents the docking mechanism from interfering with topside well access and lid placement/removal, when the plate can be engaged. The edge protrusion includes side tabs, making it compatible with automated cell culture and liquid dispensing equipment. With this configuration, the docking mechanism places all of the docking force directly on the edges of the plate, placing even pressure directly over the high-density connector interface.

Characterization

Sterilization

PCB fabrication is typically not performed in a cleanroom environment and can be prone to external contamination. Additionally material purity in PCB processes can be less stringent than traditional cleanroom processes. Toxicity from copper and nickel with potential leaching through the Kapton layer can be an additional concern. Laser micromachining of Kapton is a process that can potentially release leachants on to the surface of the electrodes. Thus, in one aspect of the present disclosure, a sterilization process is provided to alleviate any issues with cytotoxicity across multiple cell lines (e.g., rat cortical, rat hippocampal, mouse cortical, stem cell, Doral Root Ganglion (DRG) etc.) and multiple material surfaces (e.g., Kapton and SU-8).

In one aspect, sterilization of the electrophysiology culture plate comprises the use of deionized (DI) water, ethanol and heat to produce highly cytocompatible surfaces. In one aspect, the technique can involve cleaning the assembled HTMEAs in DI water (3 times) followed by an aseptic rinse in sterile 70% ethanol. Next, the device can be exposed to 70% ethanol for 5 minutes in a passive setting and rinsed in 100% ethanol immediately following this step. The electrophysiology culture plate can then be baked for 4-5 hours at 50° C. in a sterile oven and heat-sealed into plastic trays immediately after the oven bake.

Impedance Measurements

Figure 14:
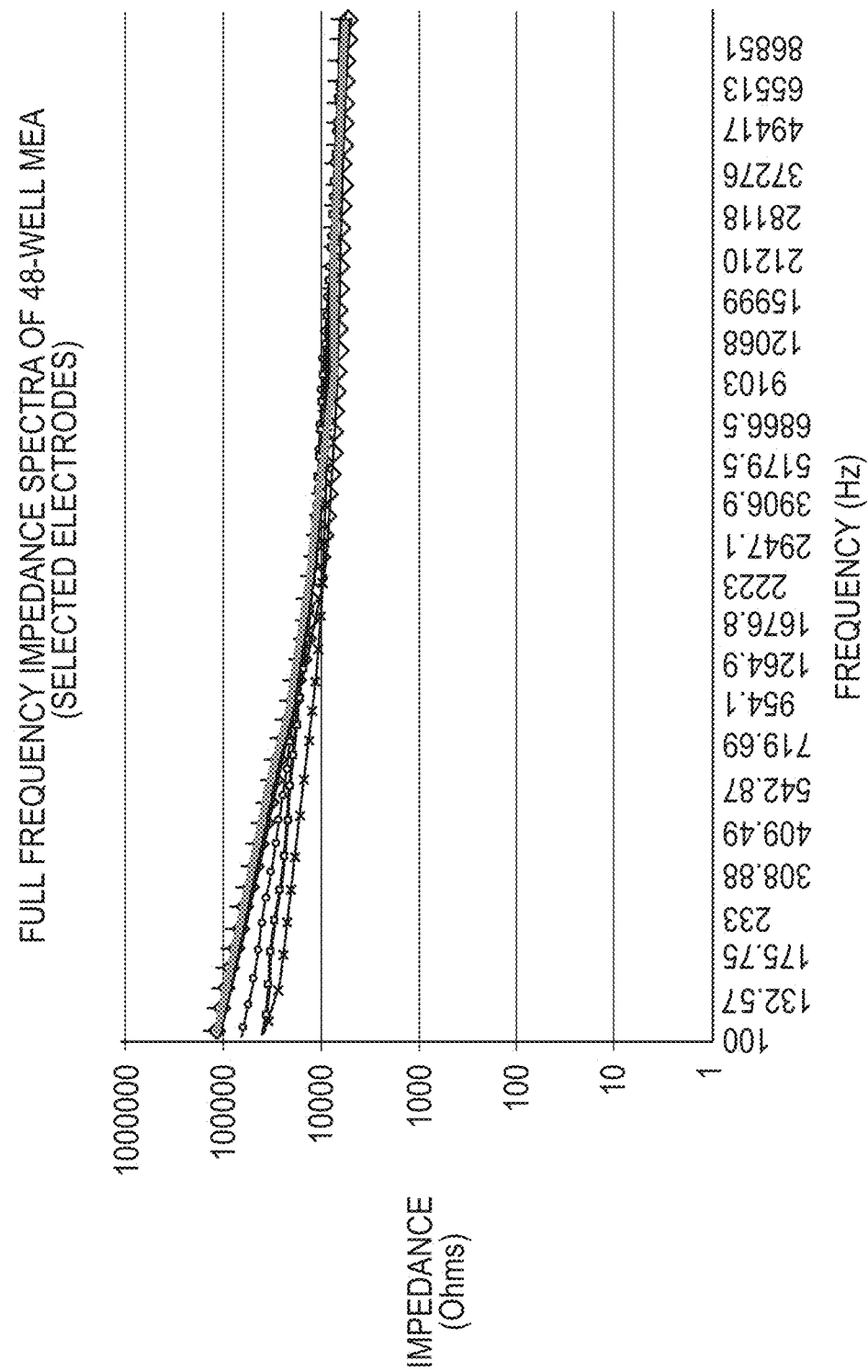
FIG. 14 shows exemplary impedance spectroscopy measurements for one representative set of nanotextured microelectrodes.

In another aspect of the present disclosure, electrical impedance spectroscopy of the fabricated electrophysiology culture plate can be used to evaluate the electrical properties of individual electrodes and can provide feedback about processing steps, such as electroplating issues or variations in the size of the microeletrodes indicating an issue with the laser micromachining process. Therefore, it can be important to establish the viability of each electrode before biological testing. In one aspect, establishing electrode viability can be accomplished with a Stanford Research SR785 (Stanford Research Systems, Sunnyvale, Calif.) two-channel dynamic signal analyzer augmented with a custom-built, controlled switching board that can allow for rapid, automated measurements of the magnitude and phase of microelectrode impedances across a large range of frequencies, e.g., 1 mHz to 100 kHz. In one illustrative example, impedance measurements can be performed between the microelectrode, a reference ground electrode and the cellular conducting media (Hank's Balanced Salt Solution), Invitrogen Corporation, Carlsbad, Calif.). Here, the fabricated and packaged 48-well electrophysiology culture plate can be interfaced with this setup and each electrode was scanned. FIG. 14 shows the impedance spectroscopy measurements of a representative set of microelectrodes out of the 768 that are distributed across the whole well. The electrodes can be well matched with an average impedance of about 70 to about 100 kOhms at 1 kHz.

Noise Measurements

Figure 15:
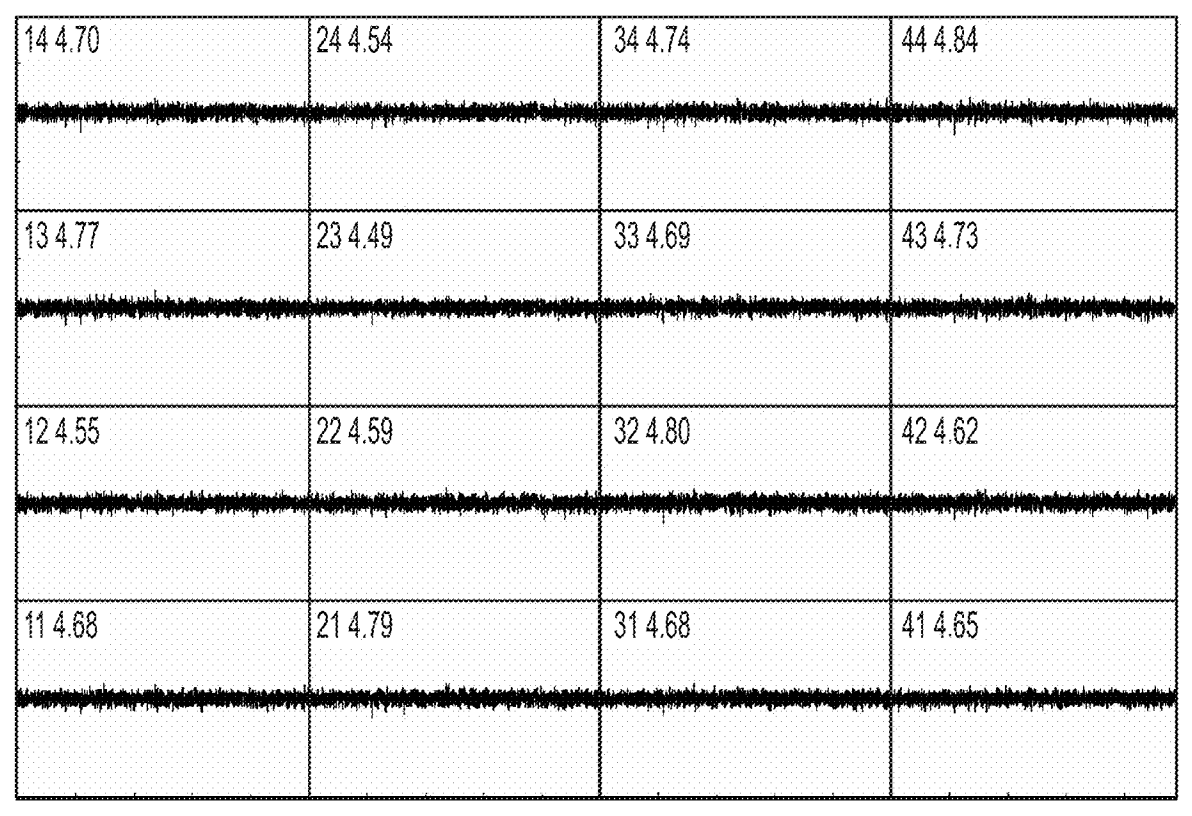

In other aspects, measurement of ambient noise of the microelectrodes can be useful for cell culture development and applications/assays the cell cultures can be used with. In light of the present disclosure, one skilled in the art will appreciate that the baseline noise of an electrode should be relatively low in order to record extracellular electrophysiological activity from an electrogenic cell culture. In one illustrative example, noise measurement was performed using the Axion Maestro System and the AxIS software. Here, the electrophysiology culture plate was interfaced with the Maestro System and measurements were made under minimum surrounding noise (e.g., no ambient lighting or blowers in hoods) between the microelectrodes, either ground or reference electrode integrated into each well, and the cellular conducting media. The baseline system noise with the nano-textured gold electrodes was measured in saline and was found to be 4-5 µV RMS (200 Hz-5 KHz), allowing for signals>10-15 µV to be consistently detected. A snap shot of the data recorded from all the channels in the electrophysiology culture plate is shown in FIG. 15, which illustrates that the RMS noise of a single well in a 48-well MEA. Here, the RMS noise lies in a range of from about 4 to about 5 microvolts ensures neural signals having a value of less than about 10 to about 15 microvolts can be consistently detected.

Cell Culture Protocols

In another aspect of the present disclosure, cell lines can be optimized for growth, survival and assay development on the electrophysiology culture plates. Here, steps for cell culture protocol development can comprise preparation of the media, preparation of the MEA surface and coating biomolecular layers on the MEA surface before plating the cells on the electrophysiology culture plates. In order to illustrate this aspect, development of rat and mouse cells lines on the electrophysiology culture plates are described below. In a further aspect, forming a cell culture protocol as described herein can be the first step toward the creation of assays.

Rat Cortical Neurons

In one aspect, a cell culture protocol is provided for rat cortical neurons. Here, E18 rat cortical neurons can be obtained in a tissue format (as a cortex pair) from commercial entities. First, the tissue can be rinsed in HBSS, pre-warmed in dilute trypsin and then broken up into a cellular suspension in a vortex. The cell suspension can then be centrifuged and individualized cells can be counted in a hemacytometer to get an accurate count of the total number of cells in suspension.

In another aspect, the media for cell growth (DMEM with glutamax and horse serum in well-established concentrations and the surface of the electrophysiology culture plates can be prepared separately. The electrophysiology culture plate is already sterilized as described previously so that it can be ready for use in an experiment upon removal from the package. The electrophysiology culture plate can be removed inside a laminar hood after wiping the edges in ethanol. Polyethylenimine (PEI) can be coated on the top surface of the MEA and incubated for 1 hour. The PEI layer can be subsequently rinsed and the MEA can be air dried in a bio safety cabinet. Laminin (prepared separately in pre-determined concentrations) can be coated on the surface of the electrophysiology culture plates and incubated. As one skilled in the art will appreciate in light of the present disclosure, the incubation integral to this step generally results in better cellular adhesion to the MEA surface. Both these biomolecular treatments can be performed in a whole area or via dotting methods. In one aspect, the whole area technique can cover the entire well whereas, in an alternate aspect, the dotting method accurately places both PEI and laminin only on the electrode area as indicated in the schematic in to ensure cell adhesion in the area of interest alone. One skilled in the art will appreciate the advantages and disadvantages to both techniques: The whole area method can be easier to implement but does incur additional resources in terms of cells and coatings while the dotting method accurately places the cells in the area of interest but can be harder to implement manually in a high-throughput format. However, the dotting method can be well-suited for automated, robotic liquid handlers that can accurately and efficiently deposit coatings/cells in a high-throughput format.

The cells can then be plated onto the MEA wells. In one aspect, the plating density depends on the application and can range from $2.5\times10^5$ cells/well and greater. The prepared media can be added to the wells immediately after the cells can be plated. The cells can be cultured in the incubator with media changes every two or three days. Electrical activity can be typically detectable in rat cortical cultures after 7 days in-vitro (DIV).

Mouse Cortical Neurons

In another aspect, a mouse cortical protocol is provided that is similar to the rat cortical protocol described above with the following modifications: Here, cryopreserved primary neuronal cells dissociated from rodent brains and spinal cords and, more particularly, E14/15 embryonic C57 mouse cortical cell line from QBM, can be utilized for these experiments. These cells can be preserved in cryo vials and, utilizing simple steps such as bringing the vial up to room temperature and adding media with monitored mixing, these cells can be prepared for plating. Here, the media used for mouse cortical cell culture can be a combination of fetal bovine serum, L-glutamine, penicillin/streptomycin and B-27 supplement into Neurobasal.

The rest of the protocol is substantially similar to that described for rat cortical cells. In light of the present disclosure, one skilled in the art will appreciate that cellular density and the biomolecular treatments can be optimized for the mouse cells. Spontaneous activity can be typically observable after 10 days in-vitro in the case of mouse cells.

Cytotoxicity Evaluation

In another aspect, the cytocompatibility of the 48-well MEA (and all the materials involved in the microfabrication and assembly of the MEA) can be measured utilizing the CellTiter-Glo Luminescent Cell Viability Assay. This assay can be a homogeneous method for determining the number of viable cells in culture based on the quantification of the Adinosine Tri-Phosphate (ATP) present. ATP is regarded as a well-established indicator of metabolically active cells. The CellTiter-Glo® Assay can be designed for use with high-throughput formats, making it ideal for automated high-throughput screening (HTS), cell proliferation and cytotoxicity assays. The homogeneous assay procedure can involve adding the single reagent (CellTiter-Glo® Reagent) directly to cells cultured in serum-supplemented medium. Cell washing, removal of medium and multiple pipetting steps are not required. The assay system is capable of detecting as few as 15 cells/well in a 384-well format in 10 minutes after adding reagent and mixing.

In this aspect, the homogeneous "add-mix-measure" format can result in cell lysis and generation of a luminescent signal proportional to the amount of ATP present. The amount of ATP can be directly proportional to the number of cells present in culture. The CellTiter-Glo® Assay generates a "glow-type" luminescent signal, which has a half-life generally greater than five hours, depending on cell type and medium used. The extended half-life eliminates the need to use reagent injectors and can provide flexibility for continuous or batch mode processing of multiple plates. The unique homogeneous format can avoid errors that can be introduced by other ATP measurement methods that require multiple steps.

Figure 16:
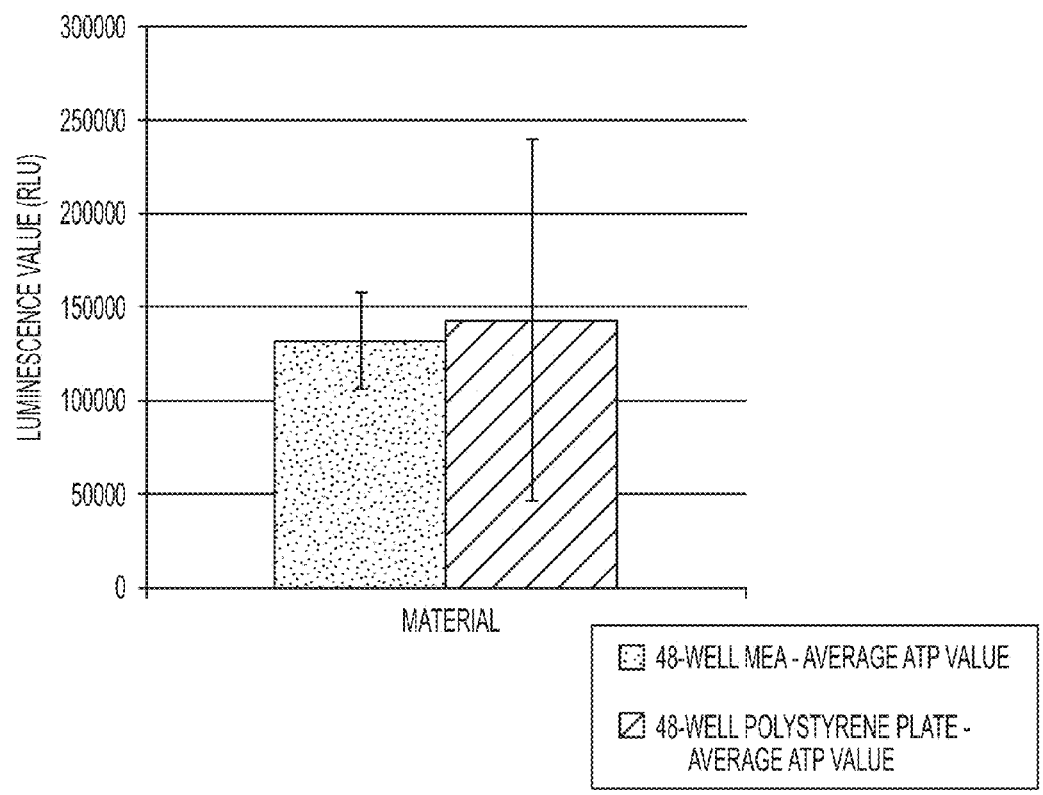
FIG. 16 depicts the cytotoxicity results of testing an electrophysiology culture plate of the present disclosure against a conventional polystyrene culture plate.
Figure 17B:
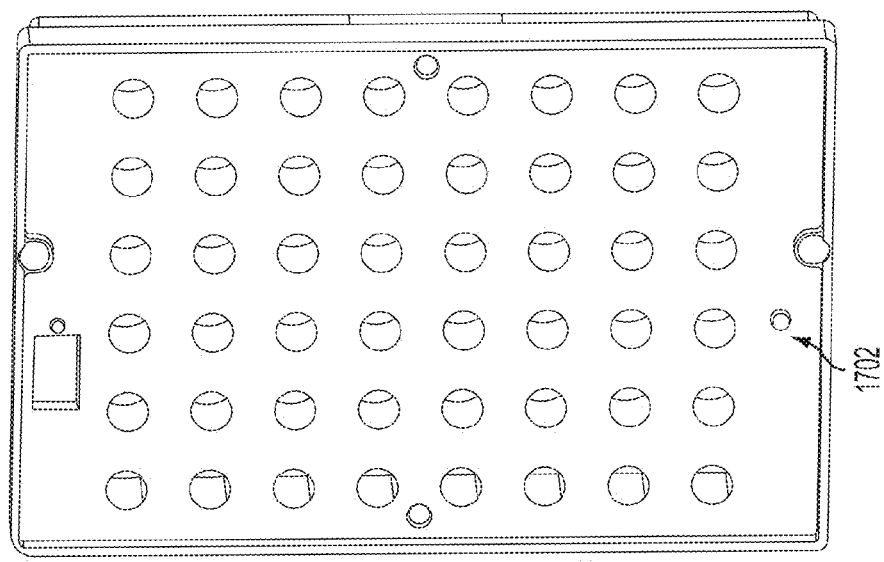
FIG. 17B shows a perspective bottom view of the MEA culture well plate of FIG. 17A.
Figure 17A:
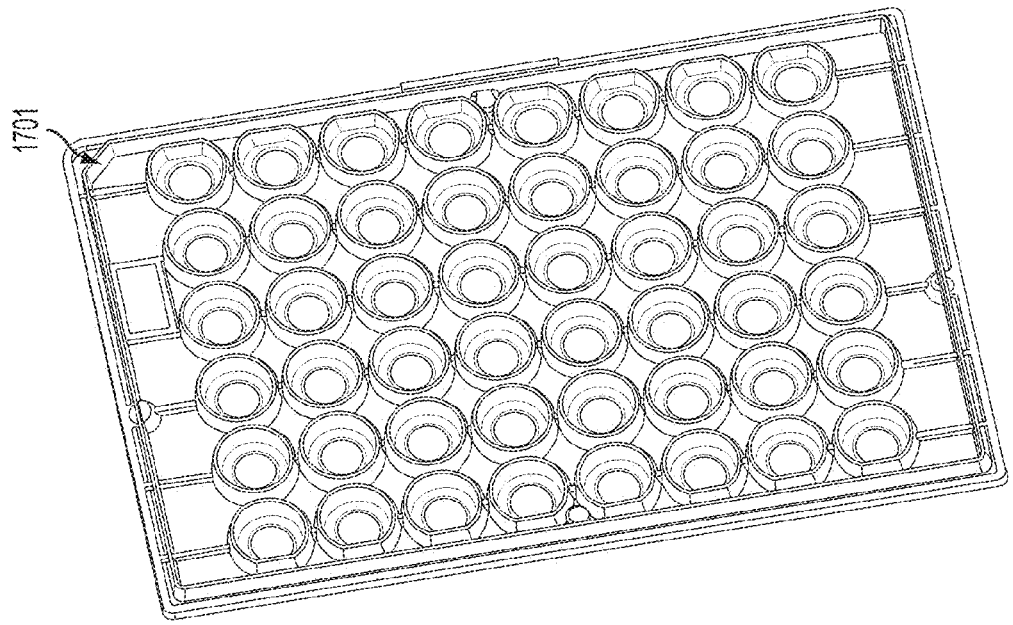
FIG. 17A shows a perspective top view of one aspect of an MEA culture well plate having alignment features, keying features and features to accommodate an IC chip.
Figure 18:
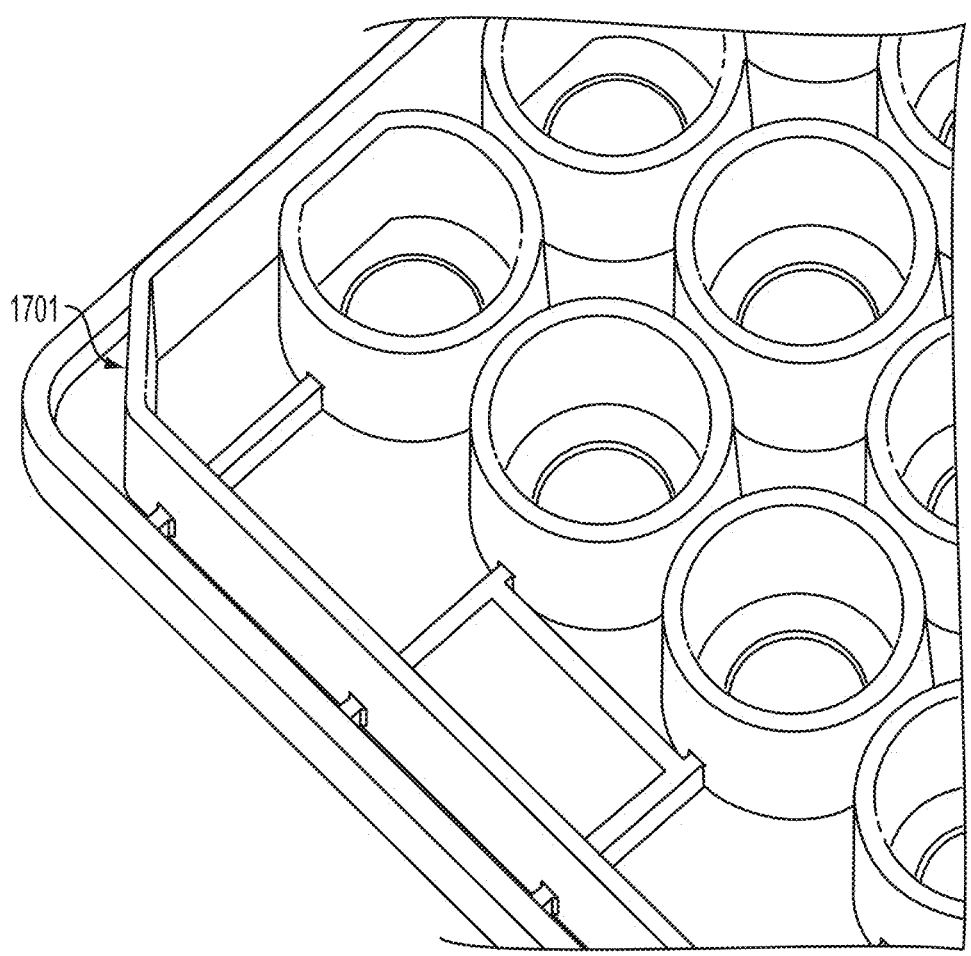
FIG. 18 shows an enlarged view of the top of MEA culture well plate of FIG. 17A.
Figure 19:
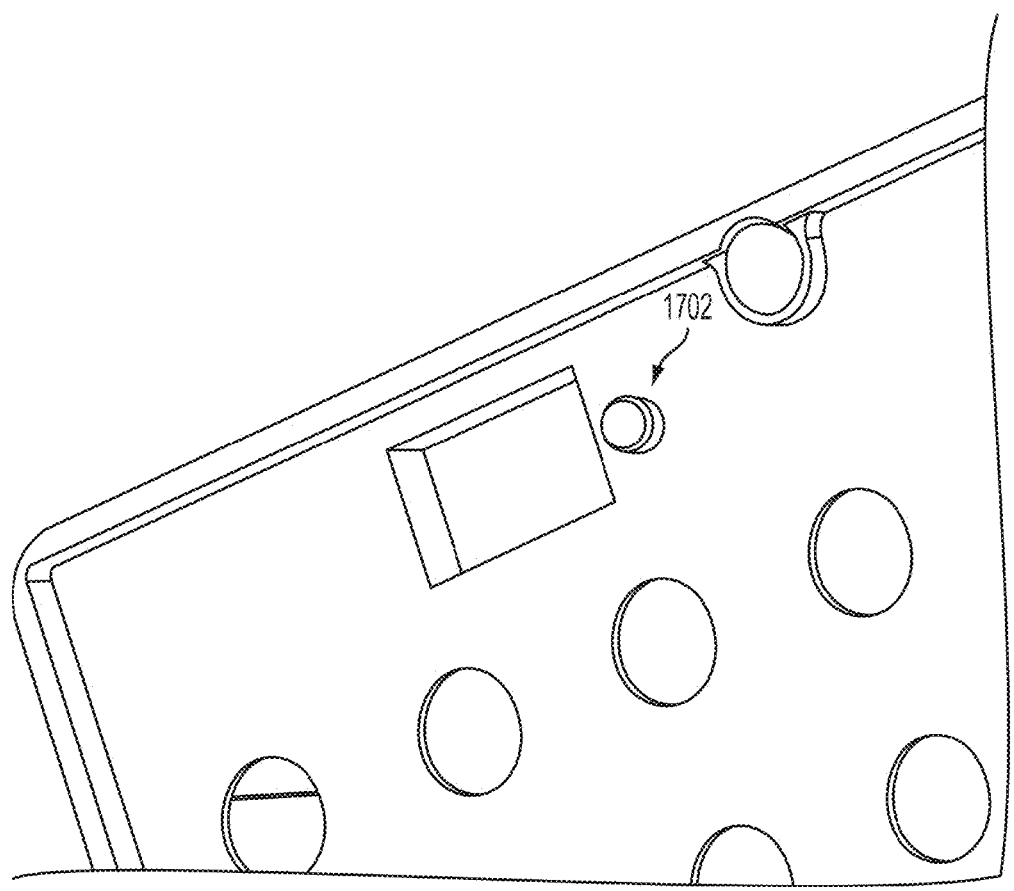
FIG. 19 shows an enlarged view of the bottom of the MEA culture well plate of FIG. 17A.

In one illustrative example, cytotoxicity evaluation of the materials involved in the fabrication of the 48-well electrophysiology culture plate, a rat cortical neuronal culture as described supra was started on multiple 48-well electrophysiology culture plates having variations in electrode sizes in order to mimick potential exposure to leachants from laser micromachining, copper or FR-4; misaligned microelectrodes in order to mimick similar issues; and normal well-aligned microelectrodes. Each of the 48-well electrophysiology culture plates were assembled and sterilized in the same manner. The effect of the potential cytotoxicity due to the various factors listed above was evaluated with an ATP assay as described above. FIG. 16 depicts practically no difference between the controls and the HTMEA wells with all the differing conditions proving excellent cytocompatibility. There were minor differences between the various 48 wells with the differing conditions. Additionally various applications discussed below establish excellent cytocompatibility with multiple cell lines at various sites worldwide.

Exemplary Uses

In other aspects, the electrophysiology culture plates of the present disclosure can be utilized for a variety of high-throughput screening applications such as, for example and without limitation, disease modeling, phenotypic screening, toxicity testing and the like. Three exemplary areas where high-throughput electrophysiology culture plates are becoming increasingly important are phenotypic screening, stem cell characterization, and toxicity/safety testing.

Phenotypic Screening

Between 1999 and 2008, despite a strong industry focus on target-based screening, the majority of first in class drugs were discovered through phenotypic screening. This success is due, in part, to the fact that discovery can be driven by desired effect, rather than an anticipated target or mechanism of action. In drug safety applications, phenotypic in vitro screening of native cell types can provide a target-agnostic approach, sensitive to acute effects that do not result in short term cytotoxicity. In neurons and other excitable cells, the most distinctive phenotype can be the action potential, and the transmission of this electrical excitation to neighboring cells.

The nature of this electrical signaling, however, presents technical challenges for established screening technologies. For example, changes in membrane voltage occur at speeds exceeding frame rates of high content imagers. Additionally, other instruments, such as high-throughput patch clamp, cannot collect measurements from multiple locations within intact networks, and thus, do not address system-level phenotypes. While neurons dissociated into in vitro cultures lack the complex organization of in vivo tissue, they do develop functional networks that display correlated activity and chemical sensitivities, strongly representative of basic properties in vivo. Moreover, neurons, cardiomyocytes, and other cell types isolated from animal disease models can display network-level disease phenotypes in vitro.

Recently, the power of phenotypic screening has been amplified by the emergence of pluripotent stem (iPS) cells induced from adult human somatic cells types. In fact, human neurons can now be differentiated in sufficient quantities for high-throughput screening platforms. Among the most enticing possibilities for human excitable cells can be the ability to screen compounds for effects on specific disease phenotypes. iPSC-derived neurons have been successfully characterized from many patients, leading to a rapidly growing bank of disease models. Using low-throughput approaches, electrophysiological phenotypes have been confirmed for a subset of these, including ALS, Rett Syndrome, fragile X syndrome, and Timothy Syndrome. In other cases, morphological or metabolic defects in patient-derived neurons strongly suggest that electrophysiological phenotypes can be observed in vitro.

Accordingly, one aspect of the present invention provides for an ideal in vitro platform for phenotypic screening of excitable networks comprising the following characteristics: (1) direct recording of the phenotypic signal of interest: voltage, (2) a signal resolution and sample rate sufficient to accurately capture action/field potentials, (3) numerous electrodes per well recorded simultaneously to assay synaptic connectivity and action potential propagation, (4) label-free, non-invasive operation to avoid perturbation of natural cell function, and, (5) preservation of cellular interconnectivity. While several current screening technologies meet a subset of these criteria, only the high-throughput electrophysiology culture plate presents a scalable solution that meets all criteria.

Stem Cell Characterization and Stem Cells as Research Tools

Stem Cell technology has accelerated rapidly in recent years. Differentiated excitable cells can be of interest for both therapy and research applications. Directing stem cell differentiation towards a specific excitable cell type can be a complex process in which the final cell type can take on undesired or unknown characteristics. As a result, such differentiated cells must be rigorously qualified. Many screening technologies exist to examine the genetic and morphological features of these cells. However, only the high-throughput electrophysiology culture plates can allow for the rapid characterization of the functional/electrophysiological behaviors of networks of excitable cells. Once such excitable differentiated cells can be characterized or qualified, they can be used as research tools (e.g., the phenotypic disease models listed in the above section.)

Toxicity and Safety Testing

The National Academy of Sciences report on "Toxicity testing in the 21st century" highlighted the need for efficient in vitro methods to screen chemicals for their potential to cause toxicity. This report proposed that high-throughput/high content in vitro screening (HTS/HCS) assays would facilitate hazard identification for thousands of chemicals for which toxicological information can be lacking Such screening approaches will need to link changes measured at the cellular or subcellular level to adverse effects through a toxicity pathway so that there can be confidence in predicting toxicological outcomes in vivo.

Many HTS/HCS endpoints assess changes in biochemical and/or cellular morphology markers, such as enzyme activity, receptor binding affinity, cell morphology, or physiological endpoints, such as regulation of intracellular calcium, sodium, membrane potential and ion channel function. When considering the problem of screening compounds for the potential to disrupt nervous system function, physiological assessment can be crucial, as disruption of ion channels, receptors and other important determinants of neuronal excitability can be key events in the toxicity pathways of many known neurotoxicants. Disruption of neuronal excitability produces substantial and rapid disruption of nervous system physiology, and often precedes or occurs in the absence of other biochemical or morphological changes. Examples include insecticides, a variety of convulsants and metals, as well as a wide range of natural toxins. However, current in vitro assays based on biochemical and morphological changes are not optimized for detecting this type of toxicity. These assays do not incorporate measurement of the key events in the toxicity pathways of such neurotoxicants (e.g. changes in intracellular ion concentrations can be secondary events), or are not amenable to collecting data at a rate that can capture the most rapid neurophysiological events, for example disruption of voltage-gated sodium channels and action potential generation by pyrethroid insecticides. By contrast, currently available electrophysiological approaches are not well designed for toxicity screening, as these assays typically consider only one potential target at a time (e.g. a particular ion channel) and often employ non-neuronal expression systems rather than neuronal tissue. Furthermore, neither biochemical nor HTS physiological (e.g. patch clamp) approaches consider chemical effects on neuronal network function. Many of these traditional assays were designed as targeted screens for pharmaceutical-lead compound development and lack the ability to detect a broad spectrum of different neurotoxicants. Thus, efficient screening assays that detect neurotoxic or neuroactive chemicals based on changes in function can be lacking, particularly those that can be sensitive to changes mediated by disruption of a variety of different toxicity pathways.

One physiological approach that addresses these limitations can be in vitro microelectrode array (MEA) recording. Using electrophysiology culture plates, spontaneous and evoked activity in neuronal networks can be recorded from a variety of different cell preparations, including primary cultures, tissue slices and intact retinas. Neuronal activity in cultures grown on electrophysiology culture plates can be sensitive to a variety of drugs and chemicals and responds to a broad spectrum of pharmaceutical compounds. As such, neuronal networks on electrophysiology culture plates can be a potential method of assessing effects of many different pharmacological classes of drugs and chemicals on nervous system function. To date, assessment of chemical effects using electrophysiology culture plates has been primarily on a chemical-by-chemical basis to understand the toxicity of individual chemicals or chemical classes Use of electrophysiology culture plates has been proposed as an in vitro neurotoxicity screening method and a recent study demonstrated consistent reproducibility and reliability of MEA measurements across five laboratories. One limitation of traditional MEA approaches can be that throughput of this methodology has been low and can be limited by the MEA plates and hardware. The disclosed disclosure overcomes such limitation to allow for comprehensive safety testing at high-throughputs.

Accordingly, FIGS. 1-23, and the corresponding text, provide a number of different devices, systems, methods and mechanisms for high-throughput electrophysiology. In addition to the foregoing, implementations described herein can also be described in terms of acts and steps in a method for accomplishing a particular result. For example, a method comprising plating, stimulating and recording data from a cell culture is described concurrently above with reference to the components and diagrams of FIGS. 1-23.

The present invention can thus be embodied in other specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. An electrophysiology culture plate comprising:
   a transparent MEA plate having:
   a substrate having a plurality of vias extending from an upper surface to a lower surface and each via being in electrical contact with each of a plurality of contact pads disposed on the lower surface,
   a first layer disposed on the upper surface of the substrate comprising a plurality of MEA arrays in electrical communication with at least a first routing layer wherein each MEA array comprises at least one reference electrode and a plurality of microelectrodes and wherein the first routing layer is in electrical communication with a select number of the plurality of vias, and
   a first insulating layer disposed on the first layer; and
   a biologic culture plate having a plurality of culture wells, wherein each culture well defines an interior cavity having a bottom surface that is at least partially transparent and is positioned in registration with a select optical port;
   wherein the transparent MEA plate underlies and is coupled to the biologic culture plate such that each MEA array is operatively coupled to one culture well of the plurality of culture wells; wherein each microelectrode and the at least one reference electrode are in electrical communication with the interior cavity of a select culture well of the plurality of culture wells through the bottom surface of the select culture well.

2. The electrophysiology culture plate of claim 1, further comprising:
   a second layer disposed on the lower surface of the substrate comprising at least a second routing layer and wherein the second routing layer is in electrical communication with a select number of the plurality of vias, and
   a second insulating layer disposed on the second layer.

3. The electrophysiology culture plate of claim 1, wherein the at least one reference electrode comprises two reference electrodes.

4. The electrophysiology culture plate of claim 3, wherein at least one of the two reference electrodes comprises two reference electrodes connected in series.

5. The electrophysiology culture plate of claim 1, wherein the biologic culture plate is bonded to the substrate.

6. The electrophysiology culture plate of claim 1, wherein the microelectrodes are nanotextured.

7. The electrophysiology culture plate of claim 1, wherein the microelectrodes are nanoporous.

8. The electrophysiology culture plate of claim 1, wherein each culture well further comprises an upper diameter and a lower diameter and wherein the lower diameter is less than the upper diameter.

9. The electrophysiology culture plate of claim 1, wherein the electrophysiology culture plate further comprises a lid configured to be selectively coupled to a peripheral edge of the biologic culture plate.

10. The electrophysiology culture plate of claim 9, wherein the lid further comprises a peripheral wall and wherein the peripheral wall is double baffled.

11. The electrophysiology culture plate of claim 9, wherein the lid comprises an individual well cap for each culture well.

12. The electrophysiology culture plate of claim 1, wherein the contact pads are positioned substantially on a peripheral region of the transparent MEA plate.

13. The electrophysiology culture plate of claim 1, wherein the biologic culture plate is configured to prevent communication of the contents of each culture well of the plurality of culture wells disposed thereon.

14. The electrophysiology culture plate of claim 1, wherein at least one of a length, a width, and a thickness of the electrophysiology culture plate conforms to at least one of American National Standards Institute standards and Society for Lab Automation and Screening standards.

15. The electrophysiology culture plate of claim 1, wherein the electrophysiology culture plate has a length of between about 127.13 to about 127.83 mm.

16. The electrophysiology culture plate of claim 1, wherein the electrophysiology culture plate has a width of between about 85.23 to about 85.73 mm.

17. The electrophysiology culture plate of claim 1, wherein the electrophysiology culture plate has a thickness of between about 14.1 to about 14.6 mm.

18. A system comprising:
an electrophysiology culture plate comprising:
a transparent monolithic MEA plate having:
a substrate having a plurality of vias extending from an upper surface to a lower surface and each via being in electrical contact with each of a plurality of contact pads disposed on the lower surface,
a first layer disposed on the upper surface of the substrate comprising a plurality of MEA arrays in electrical communication with at least first routing layer wherein each MEA array comprises at least one reference electrode and a plurality of microelectrodes and wherein the first routing layer is in electrical communication with a select number of the plurality of vias, and
a first insulating layer disposed on the first layer; and
a biologic culture plate having a plurality of culture wells, wherein each culture well defines an interior cavity having a bottom surface that is at least partially transparent and is positioned in registration with a select optical port;
wherein the transparent monolithic MEA plate underlies and is coupled to the biologic culture plate such that each MEA array is operatively coupled to one culture well of the plurality of culture wells; wherein each microelectrode and the at least one reference electrode are in electrical communication with the interior cavity of a select culture well of the plurality of culture wells through the bottom surface of the select culture well; and
an electronic unit configured to stimulate and record data from at least one microelectrode of a select MEA array, wherein the electronic unit comprises:
a receiving cavity having an interior bottom surface configured to receive the electrophysiology culture plate,
a high-density connector array disposed on the interior bottom surface of the receiving cavity configured to establish electrical contact between at least one microelectrode of the plurality of microelectrodes and the electronic unit, and
a means of exerting a predetermined force to maintain electrical contact between the contact pads disposed on the electrophysiology culture plate and the high-density connector array.

19. The system of claim 18, wherein the electrophysiology culture plate further comprises:
a second layer disposed on the lower surface of the substrate comprising at least a second routing layer and wherein the second routing layer is in electrical communication with a select number of the plurality of vias, and
a second insulating layer disposed on the second layer.

20. The system of claim 18, wherein the receiving cavity comprises at least one positioning pin extending from the interior bottom surface and the electrophysiology culture plate further comprises at least one positioning hole configured to receive the at least one positioning pin.

21. The system of claim 18, wherein the electrophysiology culture plate further comprises a lid configured to be selectively coupled to a peripheral edge of the biologic culture plate.

22. The system of claim 21, wherein the lid further comprises a peripheral wall and wherein the peripheral wall is double baffled.

23. The system of claim 21, wherein the lid comprises an individual well cap for each culture well.

24. The system of claim 21, wherein the lid is configured to be selectively removed when the electrophysiology culture plate is secured in the electronic unit.

25. The system of claim 18, wherein the electrophysiology culture plate is configured to self-align with the high-density connector array.

26. The system of claim 18, wherein the biologic culture plate is configured to prevent communication of the contents of each culture well of the plurality of culture wells disposed thereon.

27. The system of claim 18, wherein a means of exerting a predetermined force to maintain electrical contact between the contact pads disposed on the electrophysiology culture plate and the high-density connector array comprises a lever.

28. The system of claim 27, wherein the lever is configured to transmit pressure to a clamp configured to receive the electrophysiology culture plate.

29. The system of claim 18, wherein the electronic unit is configured to simultaneously stimulate and record data from at least one microelectrode of a select MEA array.

30. The system of claim 18, further comprising a heating element disposed on the interior bottom surface of the receiving cavity of the electronic unit.

* * * * *